(12) United States Patent
Short et al.

(10) Patent No.: US 10,017,741 B2
(45) Date of Patent: Jul. 10, 2018

(54) COMPOSITIONS AND METHODS FOR OBTAINING ENRICHED MESENCHYMAL STEM CELL CULTURES

(71) Applicant: StemCell Technologies Inc., Vancouver (CA)

(72) Inventors: Brenton John Short, Felixstow (AU); Christopher Duronio, Vancouver (CA)

(73) Assignee: STEMCELL TECHNOLOGIES INC., Vancouver (CA)

( * ) Notice: Subject to any disclaimer, the term of this patent is extended or adjusted under 35 U.S.C. 154(b) by 92 days.

(21) Appl. No.: 14/776,866

(22) PCT Filed: Mar. 12, 2014

(86) PCT No.: PCT/CA2014/000216
§ 371 (c)(1),
(2) Date: Sep. 15, 2015

(87) PCT Pub. No.: WO2014/138888
PCT Pub. Date: Sep. 18, 2014

(65) Prior Publication Data
US 2016/0032248 A1    Feb. 4, 2016

Related U.S. Application Data

(60) Provisional application No. 61/789,530, filed on Mar. 15, 2013.

(51) Int. Cl.
*C12N 5/0775* (2010.01)

(52) U.S. Cl.
CPC ......... *C12N 5/0663* (2013.01); *C12N 5/0668* (2013.01); *C12N 2501/727* (2013.01); *C12N 2501/999* (2013.01)

(58) Field of Classification Search
CPC .................................................. C12N 5/00
See application file for complete search history.

(56) References Cited

U.S. PATENT DOCUMENTS

2005/0265980 A1* 12/2005 Chen ................... C12N 5/0647
424/93.7

FOREIGN PATENT DOCUMENTS

WO    WO 2005/113751 A1    1/2005

OTHER PUBLICATIONS

Clanchy, Fil et la., "HUVEC co-culture and haematopoietic growth factors modulate human proliferative monocyte activity". Cytokine, Jul. 2012, vol. 59, p. 31-34.
Komohara, Y. et al. "Importance of direct macrophase-tumor cell interaction on progresson of human glioma", Cancer Sci., Dec. 2012, vol. 103, p. 2165-2172.
Mareschi, K. et al. "Multipotent mesenchymal stromal stem cell expression by plating whole bone barrow at a low cellular density: a more advantageous method for clinical use", Stem Cells Int. 2012, vol. 2012, ID 920581.
May's Technical Tip: Reducing hematopoietic contamination in MSC cultures [online]. StemCell Technologies, May 20, 2011 [retrieved on May 27, 2014]. [Retrieved from internet <URL: http://www.stemcell.com/en/News/4072a/May-Technical-Tip-Reducing-hematopoietic-contamination-in-MSC-cultures.aspx>.
Ohno, H. et al. "A c-fms tyrosine kinase inhibitor, Ki20227, suppresses osteoclast differentiation and osteolytic bone destruction in a bone metastasis model". Mol Cancer Ther. Nov. 2006, vol. 5, p. 2634-2643.
Patel, S. et al., "Colony-stimulating factor-1 receptor inhibitors for the treatment of cancer and inflammatory disease", Curr Top Med Chem., 2009 (2009), vol. 9, p. 599-610.
Hiraga T, et al. "Imatinib mesylate suppresses bone metastases of breast cancer by inhibiting osteoclasts through the blockade of c-Fms signals," Int J Cancer. Jan. 1, 2009;124(1):215-22.
Crespo O, et al. "Tyrosine kinase inhibitors ameliorate autoimmune encephalomyelitis in a mouse model of multiple sclerosis," J Clin Immunol. Dec. 2011;31(6):1010-20.
Eda H, et al. "Macrophage-colony stimulating factor and interleukin-34 induce chemokines in human whole blood," Cytokine. Dec. 2010;52(3):215-20.
Conway JG, et al. "Inhibition of colony-stimulating-factor-1 signaling in vivo with the orally bioavailable cFMS kinase inhibitor GW2580," Proc Natl Arad Sci U S A. Nov. 1, 2005;102(44):16078-83.

\* cited by examiner

*Primary Examiner* — Ruth A Davis
(74) *Attorney, Agent, or Firm* — Robin L. Teskin; LeClairRyan PLLC

(57) ABSTRACT

The disclosure provides a method of culturing cells of the mesenchymal cell lineage, said method comprising contacting the cells with a culture media comprising a CSF1R kinase inhibitor. The disclosure also provides a method of culturing cells from bone marrow and/or compact bone to enrich the cells with cells of the mesenchymal cell lineage comprising contacting the cells with a culture media comprising a CSF1R kinase inhibitor. Cell culture media comprising a CSF1R kinase inhibitor and useful for culturing cells of the mesenchymal cell lineage and/or enriching cells of the mesenchymal cell lineage is also provided.

8 Claims, 18 Drawing Sheets

A

CFU-F assay Bone Marrow

Control      1 µM GW2580

$2.5 \times 10^5$ cells $5 \times 10^5$ cells $10 \times 10^5$ cells

B

| BM CFU-F | Number of MSC colonies at day 14 | |
|---|---|---|
| Number of cells plated | Control | 1 µM GW2580 |
| $2.5 \times 10^5$ | 82 | 103 |
| $5.0 \times 10^5$ | 140 | 201 |
| $10.0 \times 10^5$ | 180 | 227 |

Passage 3 – Bone Marrow

Passage 3 – Compact Bone

Passage 3 – Compact

Passage 4 – Compact Bone

COMPOSITIONS AND METHODS FOR OBTAINING ENRICHED MESENCHYMAL STEM CELL CULTURES

CROSS-REFERENCE TO RELATED APPLICATIONS

This application is a national phase entry application of International Application No. PCT/CA2014/000216, filed Mar. 12, 2014 (which designates the U.S.), which claims the benefit of Provisional Application No. 61/789,530, filed Mar. 15, 2013, the contents of each of which are incorporated herein by reference in their entirety.

FIELD OF THE DISCLOSURE

The disclosure relates to methods of enriching for mesenchymal stem cells in mesenchymal stem cell cultures from bone marrow or compact bone. The disclosure also relates to media for said enrichment.

BACKGROUND

Bone marrow (BM) is a soft spongy tissue that resides within the hollow cavity of long bones and represents about 4% of the total body weight. It is within the BM that blood cells are produced from pluripotent hematopoietic stem cells (HSC), a process referred to as hematopoiesis. It is also within the BM and lining the wall of compact bone (CB) that mesenchymal stem cells (MSC) reside. MSC are responsible for generating various cells of the body including fibroblasts, osteoblasts, chondrocytes, adipocytes, myocytes, and endothelial cells. In addition to HSC, hematopoietic monocytes, and MSC, there are several other types of cells that reside within the BM and CB making these tissues highly heterogeneous in nature.

Bone marrow provides specific microenvironments, or niches, necessary for hematopoietic and mesenchymal stem cells, osteoblasts, endothelial and other cells to co-exist and function. It is within these niches that decisions for a stem cell to become quiescent, proliferate, differentiate, and respond to external signals take place. Recently several reports have shown that cross-talk between different stem cell niches occur in vivo to elicit a proper response in vivo (7, 8, 9, 10). It is, therefore, not surprising that BM-derived cells as well as cells lining the inner walls of CB co-exist and affect each other in in vitro culture systems. The large number of cell types and niches present in the BM and CB and the inter-association that occurs among them often translates into heterogeneous in vitro cultures that contain several successful cell types that co-exist quite well. One recurring issue with mesenchymal stem cell (MSC) cultures from BM or crushed CB is the large number of unwanted contaminating macrophages, hematopoietic and possibly other non-mesenchymal cell populations that tend to overgrow the more rare population of MSC in culture. Cultures of BM and CB-derived MSCs are often overgrown with macrophages, which frequently reside on top of the growing MSC colonies, thereby interfering with MSC proliferation and behavior in culture. This in vitro heterogeneity is often unwanted in MSC research as experimental assays are designed to study or make use of that particular cell type without the interference of others.

CSF-1 is a cytokine that oligomerizes to CSF1R leading to trans-phosphorylation of this receptor to promote cell survival, proliferation, and differentiation of mononuclear phagocyte lineages into macrophages (4, 6). Consistent with its role in regulation of macrophage lineages, exogenous CSF-1 leads to increased production of monocytes and macrophages in mice (11), while non-functional CSF-1 (12) or CSF1R (13) mice display deficient numbers of macrophages resulting in diminished inflammatory response.

One of the phenotypic characteristics of hematopoietic monocytes is the expression of CSF1R on their cell surface membrane. On these cells, activation of CSF1R leads to proliferation and differentiation. Activation of this receptor is mediated via binding of the CSF-1 ligand to the CSF1R. This oligomerization elicits an adenosine triphosphate (ATP)-dependent tyrosine kinase-mediated transduction signal that ultimately directs hematopoietic monocytes to proliferate and/or differentiate.

GW2580 [5-(3-Methoxy-4-((4-methoxybenzyl)oxy)benzyl) pyrimidine-2,4-diamine]and KI20227 {N-{4-[(6,7-dimethoxy-4-quinolyl)oxy]-2-methoxyphenyl}-N0-[1-(1,3-thiazole-2-yl)ethyl]urea} belong to a class of small molecules that specifically inhibit CSF1R kinase activity by competing with ATP binding to CSF1R kinase (14). It has been shown that GW2580 completely inhibits human CSF1R kinase at 60 nM while remaining inactive against 26 other kinases tested (3). Additionally, at 700 nM, GW2580 completely inhibited CSF-1-dependent growth of mouse myeloid cells, while a CSF-1-independent cell line, human fibroblasts, and other endothelial cells remained highly resistant to GW2580 (3).

SUMMARY

The present inventors have shown that specific inhibition of CSF1R kinase with small molecules and other compounds with similar properties in human and mouse BM and CB cell cultures reduces the number of mature macrophages in culture, which in turn, leads to an enriched culture of MSCs. Additionally, these molecules or compounds also have effects on other non-mesenchymal cells or derived progenitors present in the culture. Overall, the use of such compounds enriches for mesenchymal cells while removing or inhibiting the presence of differentiated non-mesenchymal cells.

According, the present disclosure relates to a method of culturing cells of the mesenchymal cell lineage, said method comprising contacting the cells with a culture medium comprising a CSF1R kinase inhibitor.

The disclosure also relates to a method of culturing cells from bone marrow and/or compact bone to enrich the cell culture with cells of the mesenchymal cell lineage comprising contacting the cell culture with a culture media comprising a CSF1R kinase inhibitor.

In one embodiment, the method comprises:
  a) harvesting cells from a tissue sample obtained from a subject, wherein the harvested cells comprise cells of the mesenchymal cell lineage, and
  b) contacting the harvested cells with a culture media comprising a CSF1R kinase inhibitor.

In one embodiment, the method further comprises c) obtaining a population of cells enriched for cells of the mesenchymal cell lineage.

Optionally, the CSF1R kinase inhibitor is GW2580, KI20227, HY-13075, cFMS Receptor Inhibitor II, cFMS Receptor Inhibitor III, cFMS Receptor Inhibitor IV or ARRY-382.

In another embodiment, the harvested cells further comprise non-mesenchymal cells. In a further embodiment, the non-mesenchymal cells are macrophages.

In another embodiment, the method is performed in vitro.

In another embodiment, the cells of the mesenchymal cell lineage comprise at least one of a mesenchymal stem cell, a mesenchymal cell progenitor and a stromal-derived cell.

In another embodiment, the tissue sample comprises bone marrow, compact bone, adipose tissue, or any tissue where MSCs reside.

In another embodiment, the cells are contacted with the culture media for at least one hour, at least one day or at least one week.

In another embodiment, prior to contacting the cells with the culture media, the concentration of the cells of the mesenchymal cell lineage is at least 10 cells/cm$^2$.

In another embodiment, the cells of the mesenchymal cell lineage retain their ability to form adipogenic, chrondrogenic and osteogenic cell lineages.

In one embodiment, the cells from bone marrow and/or compact bone comprise cells of the mesenchymal cell lineage and non-mesenchymal cells.

The disclosure further relates to a cell culture media useful for culturing cells of the mesenchymal cell lineage and/or enriching cells of the mesenchymal cell lineage.

In one embodiment, the cell culture media comprises a CSF1R kinase inhibitor.

In another embodiment, the CSF1R kinase inhibitor is a small molecule that inhibits CSF1R kinase activity by competing with ATP binding to CSFR1 kinase.

In another embodiment, the CSF1R kinase inhibitor is GW2580, KI20227, HY-13075, cFMS Receptor Inhibitor II, cFMS Receptor Inhibitor III, cFMS Receptor Inhibitor IV or ARRY-382. Optionally, the medium comprises 1-10 µM GW2580.

In another embodiment, the media further comprises at least one growth factor. Optionally, the at least one growth factor is selected from the list consisting of FGF, EGF and IGF.

In another embodiment, the media comprises a basal media. Optionally, the basal media is selected from Dulbecco's modified Eagles's medium (DMEM), advanced DMEM, Biogro™, SkGM™, Ham's F10, Ham's F12, Iscove's modified Dulbecco's medium, neurobasal medium, RPMI 1640 and MCDB120 medium.

In another embodiment, the media further comprises a supplement. Optionally, the supplement is selected from:
  insulin, transferring and selenite (ITS);
  B27;
  dexamethasone, insulin, EGF, fetuin and albumin; and
  dexamethasone, bFGF, albumin and insulin.

In another embodiment, the media further comprises a lipid. Optionally, the lipid is at least one of arachidonic acid, cholesterol, DL-α-tocopherol acetate, linoleic acid, linolenic acid, myristic acid, oleic acid, palmitoleic acid, palmitic acid and stearic acid.

BRIEF DESCRIPTION OF THE DRAWINGS

The disclosure will now be described in relation to the drawings in which.

Figure 1:
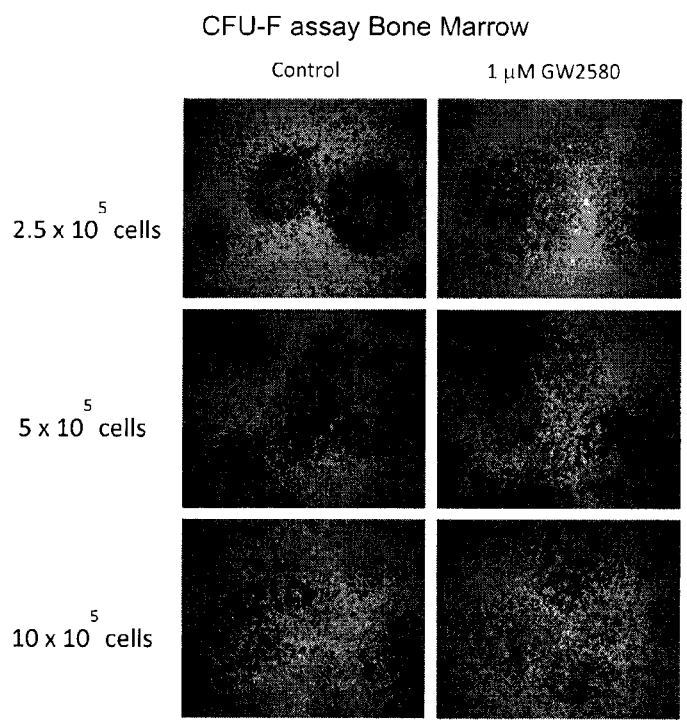
FIG. 1 shows that colony-forming units-fibroblasts (CFU-F) cultures of BM-derived cells treated with 1 µM GW2580 have reduced macrophage contamination and MSC colonies are larger in number and in size. A, Cells were seeded at the indicated densities in 6-well plates and treated with vehicle (control) or 1 µM GW2580 for 14 days. Cultures were fixed and stained with Toluidine blue and MSC CFU-F assessed. Control cultures show smaller MSC CFU-F that are overgrown with dark, heavily packed macrophages. Cultures treated with 1 µM GW2580 show larger, enriched MSC CFU-F that are mostly free of macrophages. B, Number of colonies was enumerated in both control and GW2580 treated cultures. GW2580-treated cultures show an increase of at least 20% in colony number when compared to control cultures.

Table 1 shows that addition of GW2580 to CFU-F cultures of BM- or CB-MSCs led to an increase in the number of MSC colonies in culture. Three assays were performed. In assay 1 the concentration of GW2580 used was 1 uM, whereas in assay 2 and 3, GW2580 was used at a concentration of 2.5 uM. In all assays, cultures exposed to either concentration of GW2580 for 14 days showed an overall minimal increase of 20% in the number of MSC colonies when compared to control cultures.

Table 2 shows that exposure of cultures of BM- and CB-MSC to 2.5 uM GW2580 led to a 26% (0.75 to 1.01-fold) and a 310% (0.8 to 2.46-fold) increase, respectively, in the number of CD45⁻/CD29⁺/Sca1⁺ MSCs when compared to control cultures as demonstrated by flow cytometry.

DETAILED DESCRIPTION

Methods of the Disclosure
Enriching Mesenchymal Stem Cells

The inventors discovered that small molecules and compounds that specifically inhibit CSF1R kinase prevent the proliferation and differentiation of macrophages and other hematopoietic cells, which in turn generates and expands enriched mesenchymal stem cell (MSC) cultures such as those obtained from bone marrow and crushed bone samples. The loss of differentiated mature macrophages and non-mesenchymal cells in MSC cultures allows the MSCs to expand and proliferate.

Accordingly, the disclosure provides a method of culturing cells of the mesenchymal cell lineage, said method comprising contacting the cells with a culture medium comprising a CSF1R kinase inhibitor.

The disclosure also provides a method of culturing cells from bone marrow and/or compact bone to enrich the cell culture with cells of the mesenchymal cell lineage comprising contacting the cell culture with a culture media comprising a CSF1R kinase inhibitor.

In one embodiment, the disclosure provides a method of culturing cells of the mesenchymal cell lineage comprising:

a) harvesting cells from a tissue sample of the subject, wherein the harvested cells comprise cells of the mesenchymal cell lineage and macrophages, and b) contacting the harvested cells with a culture medium comprising a CSF1R kinase inhibitor.

As used here, the term "mesenchymal stem cell" (MSC) refers to an adult stem cell traditionally found in, but not limited to, the bone marrow. MSCs can be isolated from any tissue of the body including, but not limited to, compact bone, adipose tissue, cord blood, peripheral blood, fallopian tube, fetal liver and lung. MSCs are multipotent cells found in the stroma lining of organs that are able to differentiate into a variety of cell types including osteoblasts, chondrocytes, adipocytes, tenocytes, myotubes, neural cells, and hematopoietic-supporting stroma cells. The term "cell of the mesenchymal cell lineage" refers to a cell that originated from a mesenchymal (stem or progenitor) cell. Cells of the mesenchymal cell lineage include mesenchymal stem cells, mesenchymal cell progenitors (a non-hematopoietic stem cell capable of differentiating into a mesenchymal stem cell) and stromal-derived cells. Stromal cells include all the different supporting cell types found in a given tissue or organ and are distinguished from the functional elements of the tissue or organ (the "parenchymal cells").

As used herein, the term "macrophage" refers to a cell that functions in the phagocytosis of dying or dead cells and cellular debris. Macrophages are produced by the differentiation of monocytes in tissues. They are commonly found in bone marrow and compact bone. Mature phagocytes may be identified by a C45+/CD11b+ phenotype.

As used herein, a "tissue sample" may be any sample of tissue that contains a cell of the mesenchymal cell lineage. The tissue sample may be obtained from any mammal, including, but not limited to, humans and mice. In one embodiment, the tissue sample is a bone marrow sample, a compact bone sample or a sample of adipose tissue. Preferred tissues for obtaining cells of the mesenchymal cell lineage in mice include bone marrow and compact bone. Preferred tissue for obtaining cells of the mesenchymal cell lineage in humans include bone marrow and adipose tissue.

As used herein, the term "harvesting cells" refers to isolating or extracting cells from a tissue sample such as bone marrow or compact bone. Methods of harvesting cells from tissue samples are well known in the art.

Cells harvested from bone marrow, compact bone (for example, cells lining the wall of compact bone) and adipose tissue contain mesechymal stem cells. However, the harvested cells are often contaminated with additional, unwanted cell types. Accordingly, cells harvested from bone marrow, compact bone and adipose tissue may also contain macrophages and cells of non-mesenchymal origin such as such as hematopoietic cells and fibroblasts.

The present inventors discovered that inhibitors of CSF1R kinase promotes the expansion and proliferation of cells of the mesenchymal cell lineage in cell cultures obtained from bone marrow and compact bone samples. Accordingly, the present methods include contacting cell cultures with culture medium comprising a CSF1R kinase inhibitor.

As used herein, the term "CSF1R kinase inhibitor" includes any agent, compound, small molecule or biologic that inhibits the activity of CSF1R.

Colony stimulating factor-1 (CSF-1) is a cytokine that signals through the tyrosine kinase colony stimulating factor 1 receptor (CSF1R) to stimulate cell survival, proliferation, and differentiation of mononuclear phagocytes, or macrophages.

The survival, proliferation, and differentiation of macrophages is dependent on activation of the CSF1R receptor by CSF-1. Accordingly, in one embodiment, a CSF1R inhibitor is a small molecule that specifically inhibits CSF1R kinase activity by competing with ATP binding to the CSF1R kinase receptor thereby preventing macrophage survival, proliferation, and differentiation.

In another embodiment, the CSF1R inhibitor is GW2580 [5-(3-Methoxy-4-((4-methoxybenzyl)oxy)benzyl)pyrimidine-2,4-diamine] or KI20227 {N-{4-[(6,7-dimethoxy-4-quinolyl)oxy]-2-methoxyphenyl}-N0-[1-(1,3-thiazole-2-yl)ethyl]urea}. Other CSF1R inhibitors include HY-13075 {4-cyano-N-[4-(4-methylpiperazin-1-yl)-2-(4-methylpiperidin-1-yl)phenyl]-1H-pyrrole-2-carboxamide}, cFMS Receptor Inhibitor II {4-(3,4-Dimethylanilino)-7-(4-pyridyl)quinoline-3-carboxamide}, cFMS Receptor Inhibitor III {4-(3,4-Dimethylanilino)-7-(4-(methylsulfonyl)phenyl)quinoline-3-carboxamide}, cFMS Receptor Inhibitor IV {5-Cyano-N-(2,5-di(piperidin-1-yl)phenyl)furan-2-carboxamide, CSF-1 Receptor Inhibitor IV} and ARRY-382.

The CAS numbers for a number of the compounds listed above are as follows:

| Inhibitor | CAS Number |
| --- | --- |
| GW2580 | 870483-87-7 |
| KI20227 | 623142-96-1 |
| HY-13075 | 885704-21-2 |
| cFMS Receptor Inhibitor II | 959860-85-6 |
| cFMS Receptor Inhibitor III | 959861-21-3 |
| cFMS Receptor Inhibitor IV | 959626-45-0 |

As used herein, the expression "contacting the harvested cells with a culture media" refers to any means by which the harvested cells are cultured or incubated in a culture media.

As used herein, the term "culture media" refers to media designed to support the growth of cells, in particular cells of the mesenchymal cell lineage. Various culture media are known in the art. In one embodiment, the culture media is a basal media such as Dulbecco's modified Eagles's medium (DMEM), advanced DMEM, Biogro™, SkGM™, Ham's F10, Ham's F12, Iscove's modified Dulbecco's medium, neurobasal medium, RPMI 1640 and MCDB120 medium. The medium may contain serum or be serum-free.

Optionally, the harvested cells are contacted with a culture media comprising a CSF1R inhibitor for at least an hour, at least one, three or five days, at least a week or more than one week. In another embodiment, the harvested cells are contacted with a culture media comprising a CSF1R inhibitor for at least one, two, three, four or five passages. In a further embodiment, the harvested cells are continuously contacted with a culture media comprising a CSF1R inhibitor for at least an hour, at least one, three or five days, at least a week or more than one week or for at least one, two, three, four or five passages.

In one embodiment, prior to contacting the cells with the culture media, the concentration of the cells of the mesenchymal cell lineage is at least 1, 2, 5, 10, 15 or 20 cells/cm$^2$ or about 10 cells/cm$^2$. The methods of the disclosure optionally include obtaining a population of cells enriched for cells of the mesenchymal cell lineage.

A cell population, or cell culture, is enriched for cells of the mesenchymal cell lineage when it contains a greater percentage of cells of the mesenchymal cell lineage than a control cell population. In one embodiment, a control cell population is a cell population that has not been contacted with culture medium comprising a CSF1R inhibitor.

In another embodiment, a cell population is enriched for cells of the mesenchymal cell lineage when it contains an increase in the number and/or size of mesenchymal cell colonies of compared to a control cell population.

In some embodiments, a cell population is enriched for cells of the mesenchymal cell lineage when it contains at least 5%, 10%, 20%, 50% or 75% more mesenchymal cell colonies than a control cell population.

In another embodiment, a cell population is enriched for cells of the mesenchymal cell lineage when the average size of the mesenchymal cell colonies is at least 5%, 10%, 20%, 50% or 75% larger than the average size of the mesenchymal cell colonies in a control cell population.

In another embodiment, a cell population is enriched for cells of the mesenchymal cell lineage when it contains a decreased number of macrophages compared to a control cell population. In some embodiments, a cell population is enriched for cells of the mesenchymal cell lineage when there is at least a 5%, 10%, 20%, 50% or 75% decrease in the number of macrophages in the cell population compared to a control cell population. In one embodiment, the macrophages are C45+/CD11b+ macrophages.

In another embodiment, a cell population is enriched for cells of the mesenchymal cell lineage when it contains fewer mature macrophages that have been differentiated from hematopoietic monocytes compared to a control cell population. In other words, a cell population is enriched for cells of the mesenchymal cell lineage when macrophage differentiation is suppressed and hematopoetic monocytes are maintained. A cell population may be enriched for cells of the mesenchymal cell lineage when there is at least a 5%, 10%, 20%, 50% or 75% increase in the number of hematopoetic monocytes in the cell population compared to a control cell population and/or at least a 5%, 10%, 20%, 50% or 75% decrease in the number of mature macrophages in the cell population compared to the control cell population. Hematopoietic monocytes are optionally identified by a CD45+/CD11b+/Sca1+ phenotype. Mature macrophages are optionally identified by a CD45+/CD11b+/Sca1− phenotype.

Culture Media of the Disclosure

The present disclosure also provides culture media compositions useful for culturing cells of the mesenchymal cell lineage. The culture media compositions are also useful for enriching a cell population for cells of the mesenchymal cell lineage.

In one embodiment, the culture media comprises a CSF1R kinase inhibitor. In another embodiment, the CSF1R kinase inhibitor is GW2580, KI20227, HY-13075, cFMS Receptor Inhibitor II, cFMS Receptor Inhibitor III, cFMS Receptor Inhibitor IV or ARRY-382.

Optionally, the media comprises 0.1 to 20 uM GW2580, 0.5 to 15 uM GW2580, 1 to 10 uM GW2580 or about 0.1 µM, 0.5 µM, 1 uM, 5 uM, 10 uM, 15 uM or 20 uM GW2580.

In another embodiment, the media comprises 0.1 to 20 uM KI20227, 0.5 to 15 uM KI20227, 1 to 10 uM KI20227 or about 0.1 µM, 0.5 µM, 1 uM, 5 uM, 10 uM, 15 uM or 20 uM KI20227.

In one embodiment, the culture media comprising a CSF1R kinase inhibitor allows the proliferation of cells of the mesenchymal cell lineage at a higher rate than culture media that does not comprise a CSF1R kinase inhibitor.

In another embodiment, the culture media comprises at least one growth factor. Optionally, the growth factor is FGF, EGF, IGF or bFGF or any combination thereof.

The culture media can be any culture media useful in culturing cells of the mesenchymal cell lineage. In one embodiment, the culture media comprises a basal media. Basal media are known in the art and include Dulbecco's modified Eagles's medium (DMEM), advanced DMEM, Biogro™, SkGM™, Ham's F10, Ham's F12, Iscove's modified Dulbecco's medium, neurobasal medium, RPMI 1640 and MCDB120 medium.

The culture media may be serum free or may contain serum.

In a further embodiment, the culture media comprises a supplement or a combination of supplement. Examples of supplements include, but are not limited to insulin, transferring, selenite, B27, dexamethasone, insulin, fetuin and albumin and growth factors such as FGF, EGF, IGF or bFGF. Specific combinations of supplements that may be included in the media include, but are not limited to:
    insulin, transferring and selenite (ITS);
    B27;
    dexamethasone, insulin, EGF, fetuin and albumin; and
    dexamethasone, bFGF, albumin and insulin.

In another embodiment, the culture medium further comprises a lipid. Examples of lipids include, but are not limited to, arachidonic acid, cholesterol, DL-α-tocopherol acetate, linoleic acid, linolenic acid, myristic acid, oleic acid, palmitoleic acid, palmitic acid and stearic acid.

Uses of Enriched Populations of MSCs

Enriched populations of MSCs can be obtained according to the methods described herein. Applications and uses of enriched populations of MSCs include, but are not limited to, expansion of MSCs, differentiation of MSCs into mesenchymal lineages such as osteogenic, chondrogenic, adipogenic, or myogenic lineages and differentiation of MSCs into non-mesenchymal lineages such as epithelial, cardiomyogenic, neural, or hepatogenic. The differentiated lineages can be used for both in vitro or in vivo purposes.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: Obtaining MSCs from Adult Mice

For mouse cells, the procedure involves the use of hind limbs of freshly euthanized (e.g. from 0 to 24 hours after euthanization) adult mice as a source of BM and CB-derived MSC. The hind legs of euthanized mice, including the hip bones are skinned and removed from the animals. Adjoining soft tissues and epiphyses are completely removed and scraped off the bones. Clean bones are then transferred to a mortar containing wash buffer (PBS, 2% FBS, 1 mM EDTA) and lightly crushed with a pestle to release the marrow. The wash buffer containing the marrow is transferred to a tube and the process repeated until all the marrow has been removed and the buffer is clear of red blood cells. The buffer containing the marrow is then spun down and P0 cells resuspended in expansion medium and plated at $6.7 \times 10^5$ cells/cm$^2$ (50 million cells per T75 flask) in the presence of 1 µM GW2580 for expansion of MSC, or at densities ranging from $2.5$-$10 \times 10^5$ cells/cm$^2$ in 6-well plates in the presence of 1 µM GW2580 for CFU-F assays. The crushed bones in the mortar are then transferred to a petri dish containing 2 ml of collagenase and finely minced with a scalpel. Minced bones are then digested in collagenase at 37° C. with 100 rpm circular motion for 1 hour. Digested bones are passed through a 40 µm strainer to generate a single cell solution. This strained solution is spun down at 300×g for 5 minutes, and P0 cells are resuspended in expansion medium and plated at $2.7 \times 10^4$ cells/cm$^2$ (2 million cells per T75 flask) in the presence of 1 µM GW2580 for expansion of MSC, or at densities ranging from $5$-$25 \times 10^3$ cells/cm$^2$ in 6-well plates in the presence of 1 µM GW2580 for CFU-F assays. The P0 expansion cultures of BM and CB are incubated at 37° C. in a humidified chamber at 5% $CO_2$ 5% $O_2$ for 10 to 14 days to allow for expansion and enrichment of MSC. Cultures are then passaged and plated at $6.7 \times 10^3$ cells/cm$^2$ in the presence of 1 µM GW2580 until they reach 70 to 80% confluence. Passaging is repeated every 7 days up to 10 times or until enough enriched MSCs are obtained for downstream applications. CFU-F assay cultures are fixed and stained with Toluidine blue at day 14 for colony formation assessment. For comparison purposes, control cultures for expansion and CFU-F assays are set up in the presence of DMSO vehicle instead of GW2580.

Isolation of Mouse BM and CB-Derived MSC Cells

1. A mortar and pestle were cleaned with 70% isopropanol. Isopropanol was removed from the mortar and pestle, and allowed to air dry in a sterile biohazard safety cabinet for 30 minutes. Mortar and pestle were then rinsed with sterile Phosphate Buffered Saline (PBS) just prior to use.
2. Scissors and forceps were cleaned with an alcohol wipe and allowed to air dry completely.
3. After sacrificing the mouse, the pelt was soaked thoroughly with 70% isopropanol, then clipped and peeled back to expose the hind limbs. Using sterile sharp scissors a small incision was made parallel and as close to the spine as possible. The foot was held and the leg pulled towards the head to remove the entire intact leg (Iliac Crest, femur and tibia) from the animal. The process was repeated for the remaining leg. Using a scalpel, the tibia was cut just above the ankle to remove the foot. The leg was positioned such that the iliac crest was facing up. The femur was held near the knee and the scalpel used to scrape down the femur towards the Iliac crest to dislocate the hip joint and to expose the femoral head. The remaining muscle was cut to remove the iliac crest, and the knee joint was cut in the center to remove ligaments and excess tissue.
4. Using a scalpel, bones were scraped thoroughly to remove muscle, and cut to remove epiphyses. Bones were cleaned and scraped thoroughly to ensure that no remaining muscle tissue was attached.
5. Clean bones were placed in the mortar containing 10 mL PBS with 2% FBS (STEMCELL Catalog #07905) and 1 mM EDTA. The solution of PBS with 2% FBS and 1 mM EDTA was then referred to as 'Buffer'.
6. Bones were crushed gently with pestle, using only enough force to crack open the bones. Bones were gently agitated to free bone marrow (BM) from bone fragments and the Buffer containing the marrow was transferred into a tube and kept tube on ice.
7. 10 mL fresh Buffer was added to the mortar and the bones gently crushed further followed by agitation to release the marrow as necessary and the Buffer collected into a tube. BM tube was kept on ice until all washes are done. The wash step was repeated until the majority of the BM had been removed (bone fragments turned white in color). Note that a loss of cell viability and excess debris is observed when bones are harshly ground. It is important that only gentle pressure is used to crack open the bones.
8. Bone fragments were transferred to a 100 mm dish containing 2 mL of 0.25% Collagenase Type I in PBS containing 20% FBS (STEMCELL Catalog #07902) making sure that bones were completely covered in solution. Bones were allowed to sit for 3-5 minutes in the Collagenase solution to soften the bones so they could be chopped more easily.
9. Using a scalpel, the remaining bone fragments were chopped into fine pieces (1-2 mm fragments) a proper bone fragmentation is required to release sufficient amounts of cells.
10. The bone fragments and collagenase solution were transferred to a 50 mL polypropylene tube and 0.25% Collagenase Type I (STEMCELL Catalog #07902) was added further to a final volume of 2 mL per mouse used, or a minimum of 10 mL.
11. The tube lids were sealed with Parafilm® and the tube placed in a shaking 37 C waterbath at maximum speed for 45 minutes. A bacterial culture shaker can also be used at ~200 rpm.
12. After 45 minutes, the tube was removed from the shaker and Buffer added (refer to Step 6) to a final volume of 30 mL. Supernatant was collected and filtered through a 70 µm cell strainer (Falcon, Catalog #352350). Bone fragments were washed by mixing with an additional 10 mL of Buffer and fragments allowed to settle for 3-4 minutes. The wash through was filtered through a 70 µm strainer (Falcon, Catalog #352350), and combined with the previously collected cells (for a final volume of 40 mL).
13. The BM tube from step 7 was taken and BM suspension filtered through a 70 µm cell strainer.
14. Both CB and BM tubes were centrifuged at 300×g for 10 minutes at room temperature (15-25 C) with the brake on. The supernatant was removed and the cell pellet resuspended in ~200-500 µL of Complete MesenCult™ Medium (Mouse) (STEMCELL catalog #05511). Note that small particles and debris may be visible in the cell suspension
15. Cells were place on ice until ready for use.
16. A small aliquot of cells was removed and diluted 1/20 to 1/100 in 3% Acetic Acid with Methylene Blue (Catalog #07060) and the nucleated cells counted using a hemacytometer.
17. BM and CB-derived cells were ready for expansion and CFU-F assays in the presence of GW2580, which can then be used for specific applications.

Example 2: Obtaining MSCs from Human Cells

For human cells, BM is often the preferred tissue for extraction and enrichment of MSC. These cells are obtained by Ficoll extraction to remove red blood cells. During this process, fresh BM is diluted 5:14 in isolation buffer (PBS+ 2% FBS+2 mM EDTA) and spun down at 300×g for 30 minutes. The interface layer containing the mononuclear cells is then removed and resuspended in 40 ml cold isolation buffer, which is then centrifuged again at 300×g for 10 minutes. The supernatant is removed and cells resuspended in 2 ml expansion medium and counted. These P0 cells are then resuspended in expansion medium and plated at $6.7 \times 10^5$ cells/cm$^2$ (50 million cells per T75 flask) in the presence of 1 µM GW2580 for expansion of MSC, or at densities ranging from $2.5-10 \times 10^5$ cells/cm$^2$ in 6-well plates in the presence of 1 µM GW2580 for CFU-F assays. Human BM cultures are incubated at 37° C. in a humidified chamber containing 5% $CO_2$ for 10 to 14 days to allow for expansion and enrichment of MSC. Cultures are then passaged and plated at $6.7 \times 10^3$ cells/cm$^2$ in the presence of 1 µM GW2580 until they reach 70 to 80% confluence. Passaging is repeated every 7 days up to 10 times or until enough enriched MSCs are obtained for downstream applications. CFU-F assay cultures are fixed and stained with Toluidine blue at day 14 for colony formation assessment. For comparison purposes, control cultures for expansion and CFU-F assays are setup in the presence of DMSO vehicle instead of GW2580.

Isolation of Human BM-Derived MSC Cells
Removal of Red Blood Cells
1. 500 mL Isolation Buffer was prepared (PBS+2% FBS+2 mM EDTA) using sterile components or filtering Isolation Buffer through a 0.2 micron filter. Once made, the Isolation Buffer was stored at 2-8° C.
2. The total number of nucleated cells in the BM sample was counted by taking 10 µL BM and diluting it 1/50-1/100 with 3% Acetic Acid with Methylene Blue (STEMCELL Catalog #07060). Cells were counted using a hemacytometer.
3. 50 mL Isolation Buffer was warmed to room temperature for 20 minutes prior to use and bone marrow was diluted 5/14 final dilution with room temperature Isolation Buffer (e.g. 25 mL BM was diluted with 45 mL Isolation Buffer for a total volume of 70 mL).
4. In three 50 mL conical tubes (BD Catalog #352070), 17 mL Ficoll-Paque™ PLUS (Catalog #07907/07957) was pipetted into each tube. About 23 mL of the diluted BM from step 3 was carefully layered on top of the Ficoll-Paque™ PLUS in each tube.
5. The tubes were centrifuged at room temperature (15-25° C.) for 30 minutes at 300×g in a bench top centrifuge with the brake off.
6. The upper plasma layer was removed and discarded without disturbing the plasma:Ficoll-Paque™ PLUS interface. The mononuclear cells located at the interface layer were carefully removed and placed in a new 50 mL conical tube. Mononuclear cells were resuspended with 40 mL cold (2-8° C.) Isolation Buffer and mixed gently by pipetting.
7. Cells were centrifuged at 300×g for 10 minutes at room temperature in a bench top centrifuge with the brake on. The supernatant was removed and the cell pellet resuspended in 1-2 mL cold Isolation Buffer.
8. Cells were diluted 1/50 in 3% Acetic Acid with Methylene Blue and the total number of nucleated cells counted using a hemacytometer.
9. Cells were diluted in Complete Human MesenCult®-Proliferation medium (STEMCELL catalog #05411) at a final concentration of $1 \times 10^6$ cells/mL.
10. BM-derived cells were ready for expansion and CFU-F assays in the presence of GW2580, which can then be used for specific applications.

Example 3: Preparation of Stock Solutions of CSF1R Inhibitors

To demonstrate the effectiveness of CSF1R kinase inhibitors in preventing macrophage, differentiation, proliferation, and survival in BM and CB-derived cultures of MSC, GW2580 was chosen. GW2580 [5-(3-Methoxy-4-((4-methoxybenzyl)oxy)benzyl)pyrimidine-2,4-diamine] belongs to a class of small molecules that specifically inhibits CSF1R kinase activity by competing with ATP binding to CSF1R kinase (11). It has been shown that GW2580 completely inhibits human CSF1R kinase at 60 nM while remaining inactive against 26 other kinases tested. Additionally, KI20227 {N-{4-[(6,7-dimethoxy-4-quinolyl)oxy]-2-methoxyphenyl}-N0-[1-(1,3-thiazole-2-yl)ethyl] urea}, another CSF1R kinase inhibitor, was used to demonstrate that prevention of macrophage, differentiation, proliferation, and survival in BM and CB-derived cultures of MSC is not limited to GW2580, but instead, is an activity observed with this class of CSF1R inhibitor molecules.

GW2580 ($C_{20}H_{22}N_4O_3$) was obtained from LC Labs or BioVision and its molecular weight is 366.41. Aliquots of stocks that were 1,000 times concentrated were prepared and kept at −20 C for immediate fresh use or for stability testing as follows:
10.0 mM stock: Dissolve 3.6641 mg in 1 mL of DMSO.
5.0 mM stock: Dilute 500 µL of 10.0 mM stock in 500 µL of DMSO.
2.5 mM stock: Dilute 500 µL of 5.0 mM stock in 500 µL of DMSO.
1.0 mM stock: Dilute 200 µL of 5.0 mM stock in 800 µL of DMSO.
KI20227 ($C_{24}H_{24}N_4O_5S$) was obtained from Cedarlane and its molecular weight is 480.54. KI20227 was used at 1 µM and a 1,000 times stock was prepared as follows and stored at −20 C:
1.0 mM stock: Dissolve 4.8054 mg in 1 mL DMSO, then dilute 100 µL of this stock in 900 µL of DMSO.
Pure DMSO was used as a vehicle control for untreated cultures at 0.1% of total volume.

Example 4: Assays for BM and CB-Derived Cells a. Mouse BM and CB-Derived CFU-F Assay
1. Using mouse BM-derived cells harvested as indicated in section 2), 6-well plates were seeded in duplicate at 2.5, 5.0, and 10.0×10$^5$ cells/cm$^2$ in 2 ml of Complete MesenCult™ Medium (Mouse) (STEMCELL catalog #05511) containing DMSO or 1 µM GW2580. Similarly, CB-derived cells harvested as indicated in section 2) were seeded in 6-well plates in duplicate at 5.0, 10.0, and 25.0×10$^3$ cells/cm$^2$ in 2 ml of Complete MesenCult™ Medium (Mouse) containing DMSO or 1 µM GW2580.
2. Cultures were incubated for 10-14 days under normal (5% $CO_2$) or hypoxic conditions (5% $CO_2$/5% $O_2$) at 37 C in a cell culture incubator until colonies developed.
3. Medium was removed cultures washed with 2 mL PBS.
4. Cells were fixed by adding 2 mL methanol/well and incubated at room temperature for 5 minutes.
5. Methanol was removed and plates allowed to air dry for 5 minutes.
6. To each well, 2 mL Toluidine blue solution was added and incubated for 30 minutes at room temperature.
7. Toluidine blue solution was removed and wells rinsed with water.
8. Water was removed and plates allowed to dry.
9. Colony formation was assessed by enumeration and colony size.

b. Human BM-Derived CFU-F Assay
1. Human BM-derived cells harvested as indicated in section 3) were seeded in 6-well plates in duplicate at 2.5, 5.0, and 10.0×10$^5$ cells/cm$^2$ in 2 ml of Complete MesenCult™ Medium (Human) (STEMCELL catalog #05411) containing DMSO or 1 µM GW2580.
2. Cultures were incubated for 10-14 days under 5% $CO_2$ at 37 C in a humidified cell culture incubator until colonies developed.
3. Medium was removed and cultures washed with 2 mL PBS.
4. Cells were fixed by adding 2 mL methanol/well and incubated at room temperature for 5 minutes.
5. Methanol was removed and cultures allowed to air dry for 5 minutes.
6. To each well, 2 mL Toluidine blue solution was added and incubated for 30 minutes at room temperature.
7. Toluidine blue solution was removed and wells rinsed with water.
8. Water was removed and plates allowed to dry.
9. Colony formation was assessed by enumeration and colony size.

c. Expansion of Human BM and Mouse BM and CB-Derived Cells Assay
1. Expansion assays for mouse BM and CB-derived cells, and for human BM-derived cells were performed by seeding 5×10$^7$ cells per T75 flask at P0 for mouse and human BM-derived cells, and 2×10$^6$ cells per T75 flask at P0 for mouse CB-derived cells in complete MesenCult™ Medium (Human or Mouse medium) containing DMSO or 1 µM GW2580.
2. Cultures were allowed to grow for 10-14 days until adherent cells achieved 70 to 80% confluence. Mouse cultures were maintained under normal (5% $CO_2$) or hypoxic conditions (5% $CO_2$/5% $O_2$) at 37 C in a cell culture incubator. Human cultures were maintained under 5% $CO_2$ at 37 C in a humidified cell culture incubator.
3. Adherent cells were passaged by releasing cultures from flask. Cultures were washed with 5 mL PBS and then 5 mL of 0.25% trypsin solution (STEMCELL catalogue #07901) was added and the flasks incubated for 10 min at 37 C. To each flask, 5 mL complete medium was added to stop trypsin activity.
4. Released cells were collected into a tube and centrifuged at 300×g for 5 minutes.
5. Cells were resuspended in 2 mL of medium and counted using a hemocytometer.
6. Passage 1 (P1) cultures were setup by seeding 1.5 to 3.0×10$^3$ cells/cm$^2$ in 6-well plates or T75 flasks containing 2 or 12 mL of complete medium, respectively, containing DMSO or 1 µM GW2580.
7. P1 cultures were incubated until they reached 70 to 80% confluence.
8. Passaged cultures can be used at any time from P0 to P10 as needed for different applications.

d. Flow Cytometry Analysis
1. Cultures of BM and CB-derived cells were trypsinized for 10 minutes and an equal volume of complete medium was added to cultures to stop trypsin activity
2. Cell suspension was filtered through a 40 µm strainer, and cells counted using a hemocytometer
3. Suspension was spun down at 300×g for 5 minutes.
4. Supernatant was removed and cell pellet resuspended in FACS buffer (PBS with 2% FBS and 1 mM EDTA)
5. A total of 1×10$^5$ cells in 300 µL FACS buffer was used for each flow cytometry analysis tube, including unstained, viability, compensation, and isotype controls.
6. Cell suspensions were stained with fluorophore-labeled antibodies against CD45, CD11b, and Sca1, CD29, and viability dye.
7. Cell suspensions were analyzed on a flow cytometer using compensation and isotype control to determine laser voltage and gating.
8. Samples were gated on viable CD45$^+$ cells and 10,000 events per sample were collected. Alternatively, cells were gated on viable CD45$^-$ cells and out of this gate the proportion of CD29+/Sca1$^+$ cells obtained.

Example 5: CFU-F Assays of Mouse BM-Derived Cells Show an Increase in Number and Size of MSC Colonies and a Reduction in Macrophage Contamination when Cultures are Exposed to 1 µM GW2580

Mouse BM-derived cells were isolated as described previously and CFU-F assays setup as described above. Assays were maintained in medium containing 0.1% v/v DMSO as control or 1 µM GW2580 for 14 days. Cultures were then stained with Toluidine blue and colony formation and appearance assessed.

In cultures treated with 1 µM GW2580, the MSC colonies observed are bigger in size and have a much reduced number of macrophages when compared to control cultures. Macrophages, in control cultures, appear as small, dark, and heavily packed cells growing on top of the MSC colonies. The difference in colony size is most apparent in lower density cultures where individual colonies have clear boundaries and do not grow into each other (FIG. 1, A). In addition, Cultures treated with 1 µM GW2580 have at least 20% more colonies than control cultures (FIG. 1, B).

These results indicate that MSC support macrophage growth, which in turn interferes with CFU-F formation. Treatment of these cultures with 1 µM GW2580, on the other hand, leads to a reduction in the number of macrophages in culture and an increase in MSC colony size and number.

Example 6: CFU-F Assay of Mouse CB-Derived Cells Shows an Increase in Number and Size of MSC Colonies and a Reduction in Macrophage Contamination when Cultures are Exposed to 1 μM GW2580

Mouse CB-derived cells were isolated as described previously and CFU-F assays setup as described above. Assays were maintained in medium containing 0.1% v/v DMSO as control or 1 μM GW2580 for 14 days. Cultures were then stained with Toluidine blue and colony formation and appearance assessed.

Figure 2:
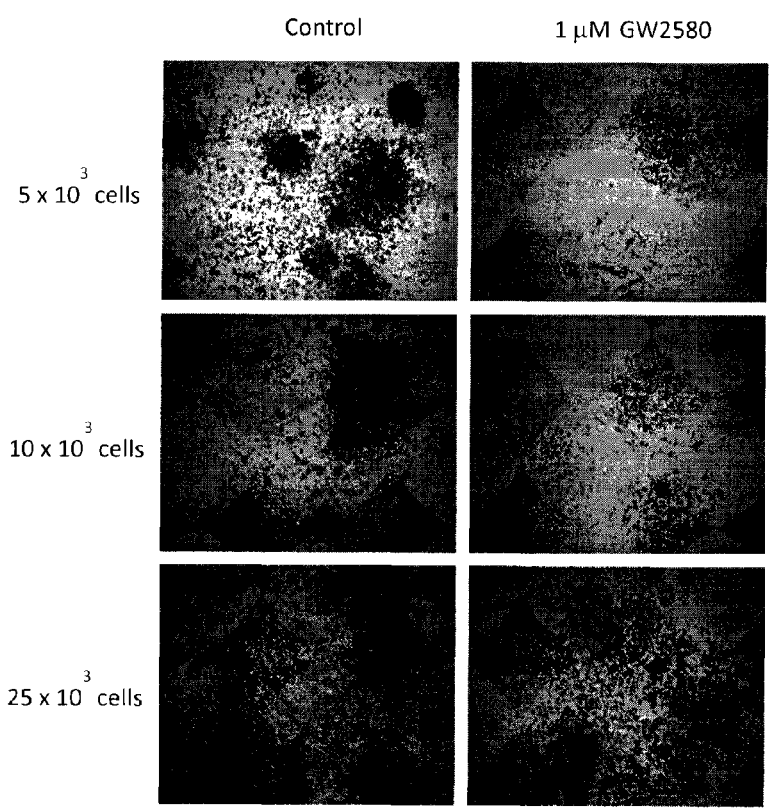
FIG. 2 shows that CFU-F cultures of CB-derived cells treated with 1 µM GW2580 have reduced macrophage contamination and MSC colonies are larger in number and in size. A, Cells were seeded at the indicated densities in 6-well plates and treated with vehicle (control) or 1 µM GW2580 for 14 days. Cultures were fixed and stained with Toluidine blue and MSC CFU-F assessed. Control cultures show smaller MSC CFU-F that are overgrown with dark, heavily packed macrophages. Cultures treated with 1 µM GW2580 show larger, enriched MSC CFU-F that are mostly free of macrophages. B, Number of colonies was enumerated in both control and GW2580 treated cultures. GW2580-treated cultures show an increase of at least 24% in colony number when compared to control cultures.

In cultures treated with 1 μM GW2580, the MSC colonies observed are bigger in size and have a much reduced number of macrophages when compared to control cultures. Macrophages, in control cultures, appear as small, dark, and heavily packed cells growing on top of the MSC colonies. The difference in colony size is most apparent in lower density cultures where individual colonies have clear boundaries and do not grow into each other (FIG. 2, A). In addition, Cultures treated with 1 μM GW2580 have at least 24% more colonies than control cultures (FIG. 2, B).

These results indicate that MSC support macrophage growth, which in turn interferes with CFU-F formation. Treatment of these cultures with 1 μM GW2580, on the other hand, leads to a reduction in the number of macrophages in culture and an increase in MSC colony size and number.

Example 7: Expansion of Mouse Cultures of Both BM and CB-Derived Cells Shows a Significant Reduction in the Number of Macrophage Contamination when Cultures are Treated with 1 μM GW2580

BM and CB-derived cultures were isolated as described above and expansion assays setup as described above. Assays were maintained in medium containing 0.1% v/v DMSO as control or 1 μM GW2580. Flow cytometry analysis was performed at P1 and images collected at P2.

Figure 3:
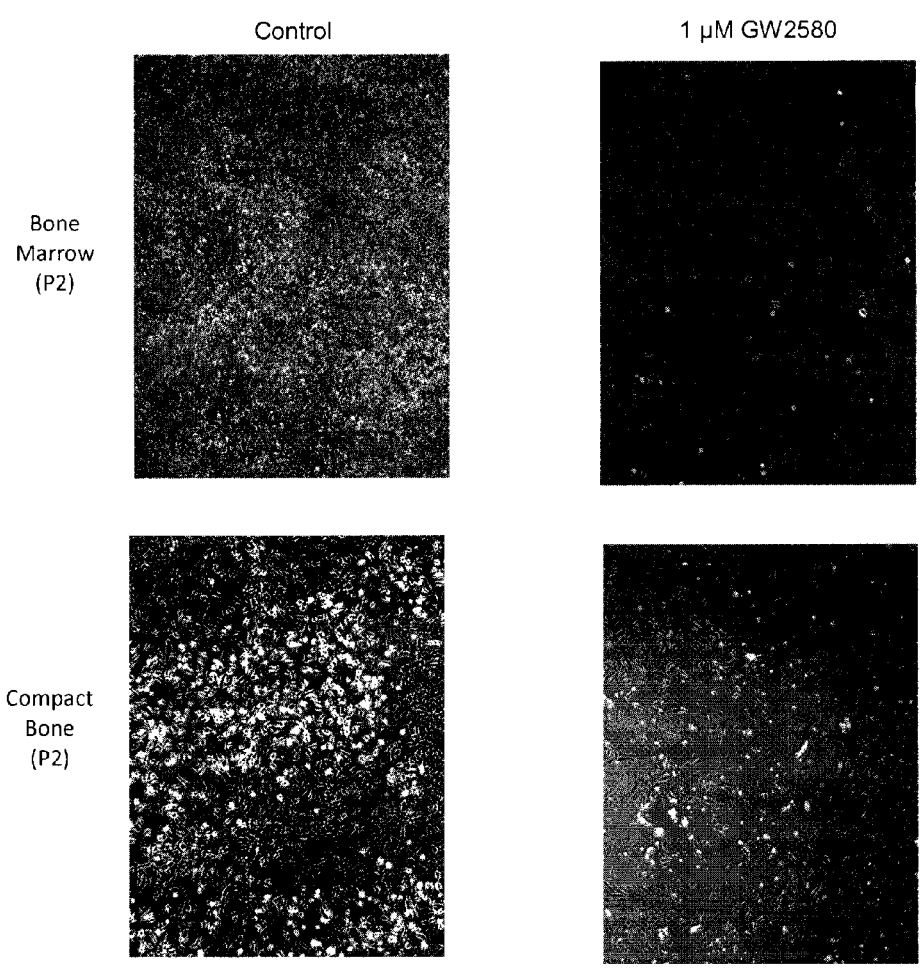
FIG. 3 shows that MSC cultures derived from BM or CB and treated with 1 µM GW2580 show a decrease in macrophages contamination, and are enriched for MSC. Control untreated cultures of both BM and CB at passage 2 (P2) are overgrown with macrophages (small, highly refractile cells), while MSC cultures treated with 1 µM GW2580 are enriched and mostly devoid of macrophage contamination.

Analysis of cultures of both BM and CB-derived cells shows that control cultures were overgrown with macrophages seen as small highly refractile cells. In cultures treated with 1 μM GW2580, however, a much reduced number of macrophages is observed and the adherent cells present display a fibroblastic morphology characteristic of MSC (FIG. 3).

Figure 4:
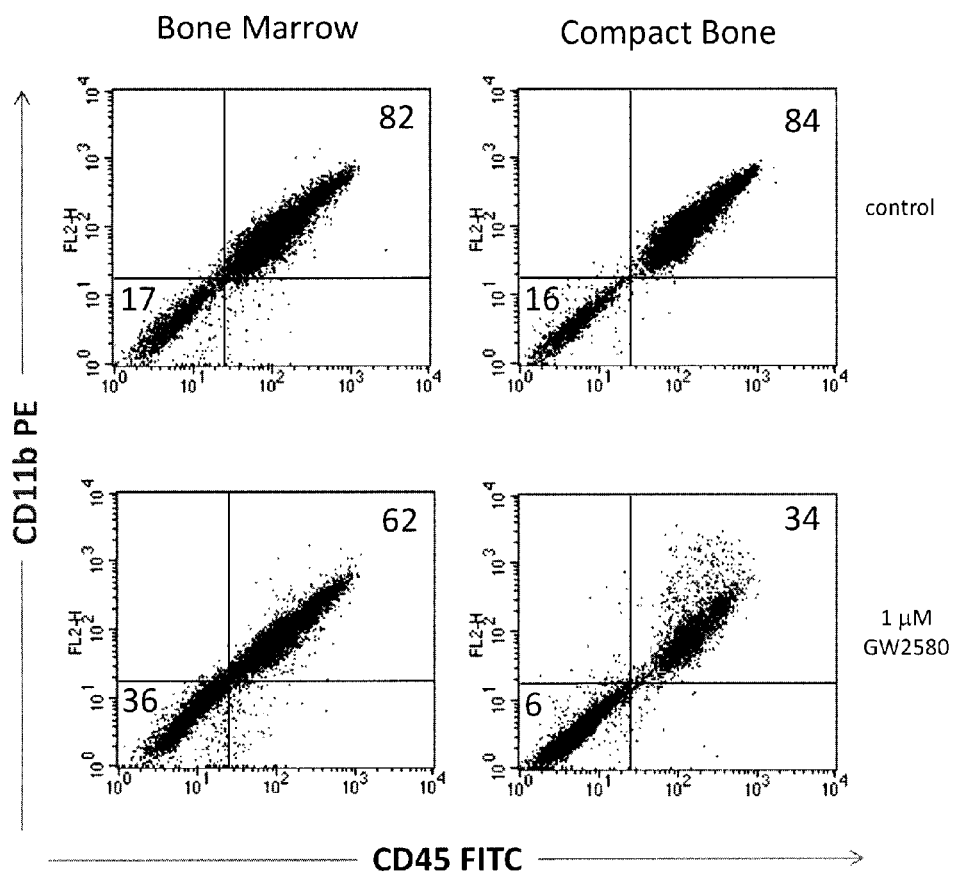
FIG. 4 shows that exposure of BM and CB-derived MSC cultures to 1 µM GW2580 leads to a 20% and 50% reduction in macrophages, respectively, at P1. Flow cytometry analysis of P1 cultures of BM that were exposed to 1 µM GW2580 indicates that 62% of the total viable cells were composed of CD45$^+$/CD11b$^+$ mature macrophages. In BM control cultures this population was 82% of the total viable cells, thus representing a 20% reduction in macrophages in GW2580-treated cultures. Likewise, treatment of CB cultures with 1 µM GW2580 indicates that these cultures were comprised of 34% CD45$^+$/CD11b$^+$ mature macrophages, representing a 50% decrease from control cultures, which contained 84% macrophages.

Flow cytometry analysis was performed as indicated in above. Samples were gated on viable cells, and analysis shows that in control BM-derived cultures 82% of the cells are $CD45^+/CD11b^+$ mature macrophages, while BM-derived cultures that were treated with 1 μM GW2580 are composed of 60% $CD45^+/CD11b^+$ mature macrophages. In CB-derived cultures, 84% of the cells are $CD45^+/CD11b^+$ mature macrophages in control cultures. This number decreases to 34% in CB-derived cultures treated with 1 μM GW2580. These results indicate that in BM-derived cultures there is a 20% reduction in mature macrophages in cultures treated with 1 μM GW2580, whereas in CB-derived cultures this reduction in mature macrophages reaches 50% (FIG. 4).

These results indicate that addition of 1 μM GW2580 to BM and CB-derived cells greatly reduces the number of macrophages in these cultures, thereby enriching the MSC population.

Example 8: Continuous Exposure of Expansion Cultures of Mouse BM-Derived Cultures to 1 μM GW2580 for at Least 3 Passages Leads to Increased Enrichment of the MSC Population while Greatly Reducing Differentiation of Contaminating Macrophages BM-derived cultures were isolated as described above and expansion assays setup as described above. Assays were maintained in medium containing 0.1% v/v DMSO as control or 1 μM GW2580 for passages P0 to P3. Images were acquired for at each passage and they show that control cultures are overgrown with contaminating macrophages at each passage time. Cultures treated with 1 μM GW2580, however, have reduced numbers of macrophages and most of the adherent cells in culture display a fibroblastic morphology typical of MSC (FIG. 5).

Figure 6:
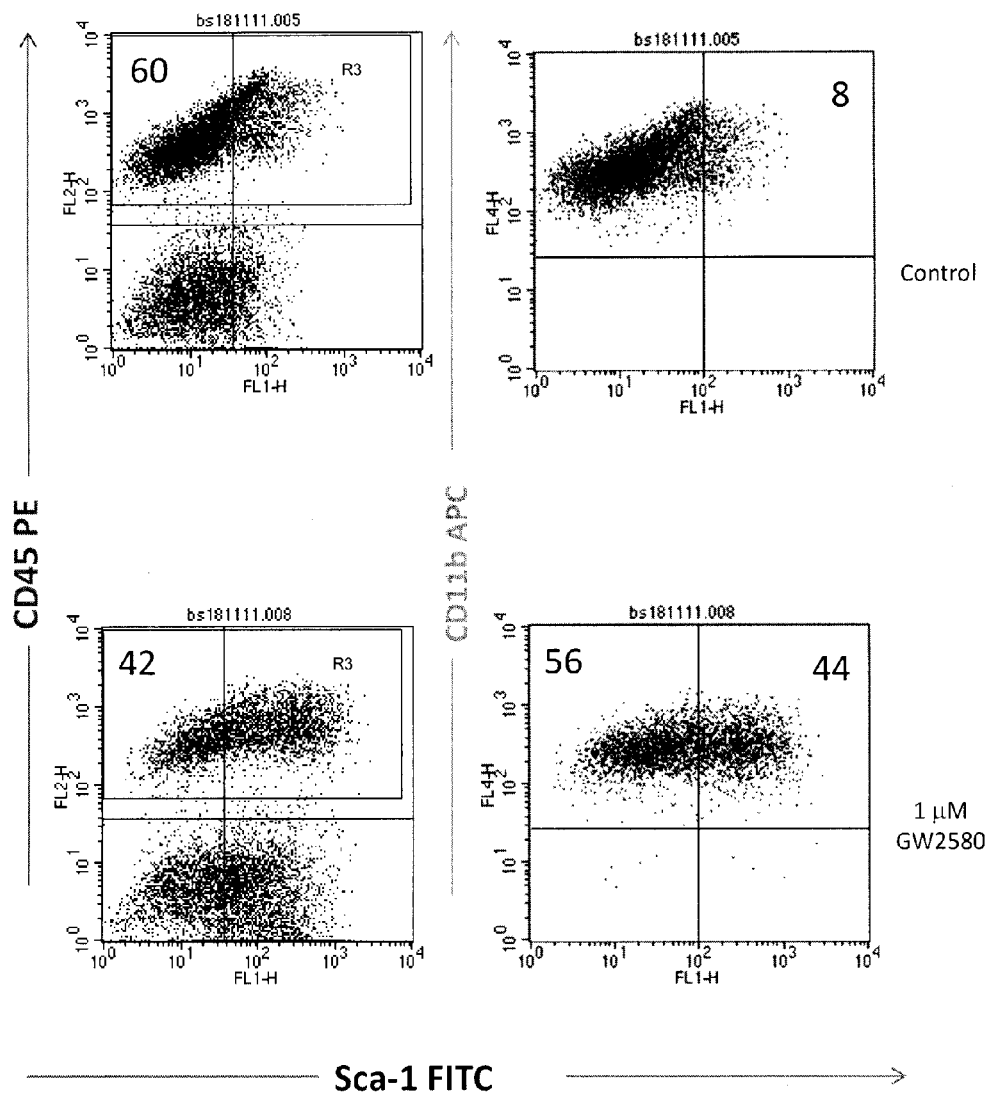
FIG. 6 shows that exposure of BM-derived cultures to 1 µM GW2580 from P0 to P2 leads to an overall 18% reduction in CD45$^+$ cells and a 36% reduction in CD45$^+$/CD11b$^+$/Sca1$^+$ monocyte differentiation into CD45$^+$/CD11b$^+$/Sca1$^-$ mature macrophage as demonstrated by flow cytometry analysis. Cultures were gated on CD45$^+$ cells and, out of this population, expression of CD11b and Sca1 was analyzed. In control cultures, 92% of the CD45$^+$ cells were also CD11b$^+$ (mature macrophages) and 8% of the cells were CD11b$^+$/Sca1$^+$. In GW2580-treated cultures, 56% of the CD45$^+$ cells were CD11b$^+$/Sca1$^-$ and 44% of the cells were CD11b$^+$/Sca1$^+$, thus suggesting that 36% of hematopoietic monocytes did not differentiate into macrophages when compared to control cultures.
Figure 7:
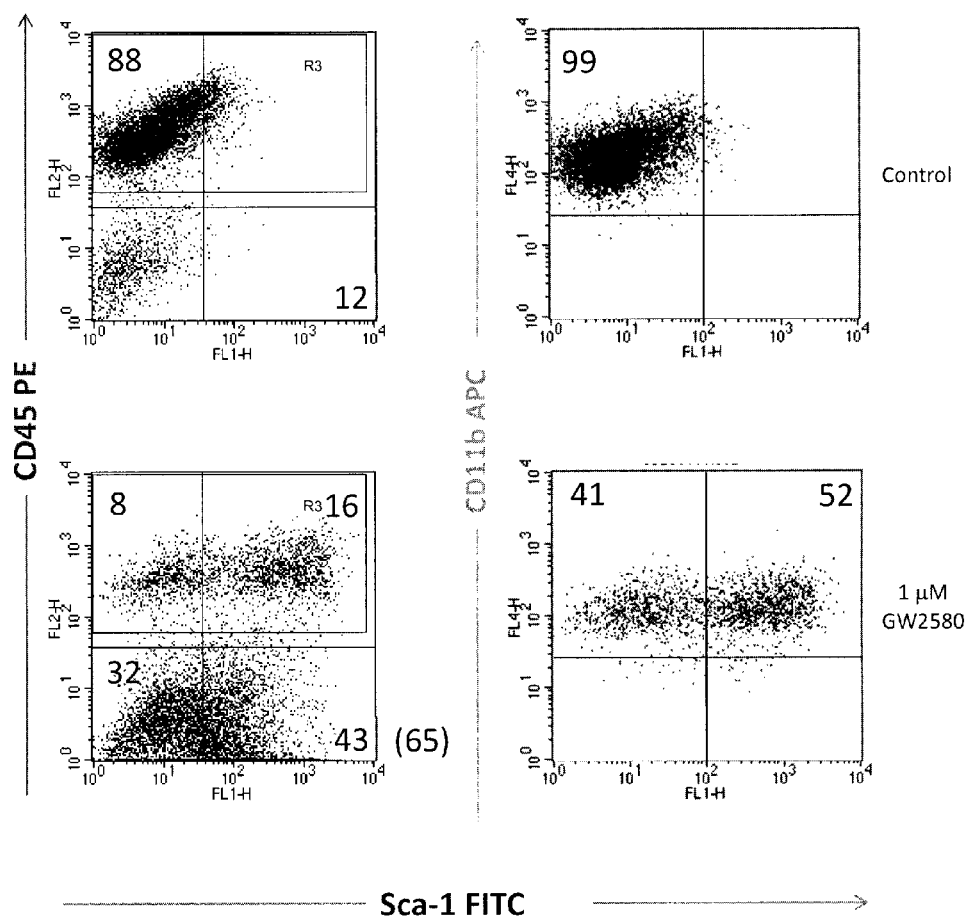
FIG. 7 shows that exposure of BM-derived cultures to 1 µM GW2580 from P0 to P3 leads to an overall 64% reduction in CD45$^+$ cells and a 52% reduction in CD45$^+$/CD11b$^+$/Sca1$^+$ hematopoietic monocyte differentiation into CD45$^+$/CD11b$^+$/Sca1$^-$ macrophages as demonstrated by flow cytometry analysis. Cultures were gated on CD45$^+$ cells and, out of this population, expression of CD11b and Sca1 was analyzed. In control cultures, 99% of the CD45$^+$ cells were also CD11b$^+$ (differentiated macrophages) and <1% of the cells were CD11b$^+$/Sca1$^+$ hematopoietic monocytes. In GW2580-treated cultures, 41% of the CD45$^+$ cells were CD11b$^+$/Sca1$^-$ and 52% of the cells were CD11b$^+$/Sca1$^+$, thus suggesting that 52% of monocyte progenitors did not differentiate into macrophages when compared to control cultures.

Flow cytometry analysis was performed as indicated above. Samples were gated on viable $CD45^+$ cells and analysis of BM-derived cultures at P2 demonstrated that in control cultures, 92% of the $CD45^+$ cells are also $CD11b^+$ mature macrophages, and only 8% maintain a $CD45^+/CD11b^+/Sca1^+$ hematopoietic monocyte phenotype. Cultures treated with 1 μM GW2580, show that 56% of $CD45^+$ cells are also $CD11b^+$ mature macrophages, and that 44% of them maintain a $CD45^+/CD11b^+/Sca1^+$ hematopoietic monocyte phenotype. Thus, these results indicate that in BM-derived cultures treated with 1 μM GW2580, there is a 36% increase in $CD45^+/CD11b$ that were also $Sca1^+$. This suggests that treatment of these cultures with 1 μM GW2580 prevented macrophage differentiation ($CD45^+/CD11b^+/Sca1^-$) while maintaining these cells as hematopoietic monocyte $CD45^+/CD11b^+/Sca1^+$ (FIG. 6). At P3, treatment of these cultures with 1 μM GW2580 led to a >50% reduction in $CD45^+/CD11b^+/Sca1^-$ mature macrophage differentiation and a similar increase in $Sca1^+$ cells. These results suggest that treatment of BM-derived cultures with 1 μM GW2580 prevented more than 50% of $CD45^+/CD11b^+/Sca1^+$ hematopoietic monocytes from differentiating into $CD45^+/CD11b^+/Sca1^-$ mature macrophages when compared to control cultures (FIG. 7).

Figure 5:
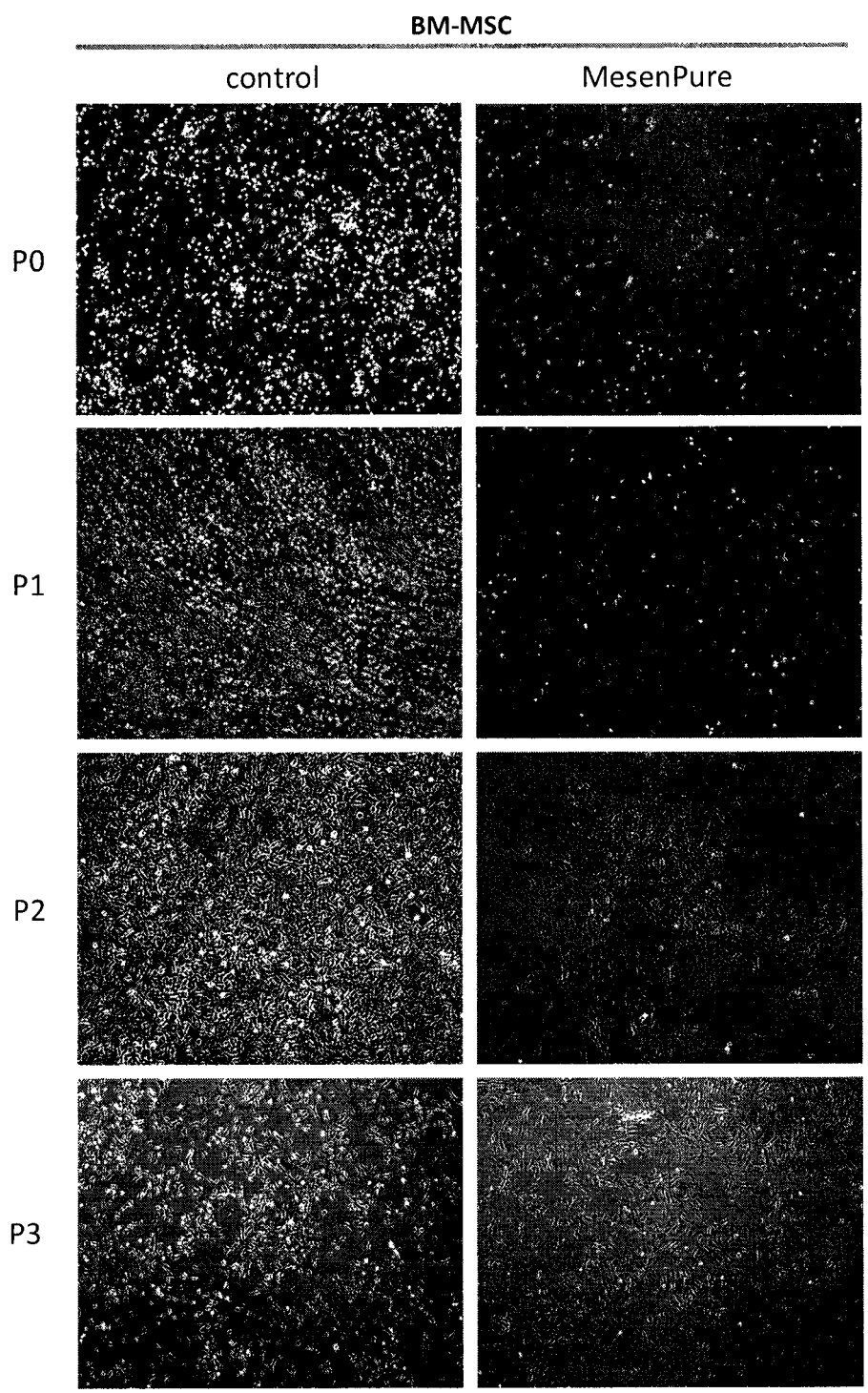
FIG. 5 shows that continuous treatment of BM cultures with 1 µM GW2580 throughout passages (P0-P3) greatly reduces the number of macrophages while maintaining an enriched population of MSC. Control cultures show a high number of small, refractile contaminating macrophages, whereas cultures treated with 1 µM GW2580 contain a much reduced number of these contaminating macrophages. In addition, GW2580-treated cultures display more abundant numbers of fibroblast-like cells that are characteristic of MSC.

Taken together, these results demonstrate that treatment of BM-derived cultures with 1 μM GW2580 prevented differentiation of $CD45^+/CD11b^+/Sca1^+$ hematopoietic monocytes into $CD45^+/CD11b^+/Sca1^-$ mature macrophages (FIGS. 6 and 7), which in turn resulted in an enriched MSC culture (FIG. 5).

Example 9: Continuous Exposure of Expansion Cultures of Mouse CB-Derived Cultures to 1 μM GW2580 for at Least 3 Passages Leads to Increased Enrichment of the MSC Population while Greatly Reducing Differentiation of Contaminating Macrophages CB-derived cultures were isolated as described above and expansion assays setup as described above. Assays were maintained in medium containing 0.1% v/v DMSO as control or 1 μM GW2580 for passages P0 to P3. Images were acquired at each passage and they show that control cultures are overgrown with contaminating macrophages at each passage time. Cultures treated with 1 μM GW2580, however, have reduced numbers of macrophages and most of the adherent cells in culture display a fibroblastic morphology typical of MSC (FIG. 8).

Figure 9:
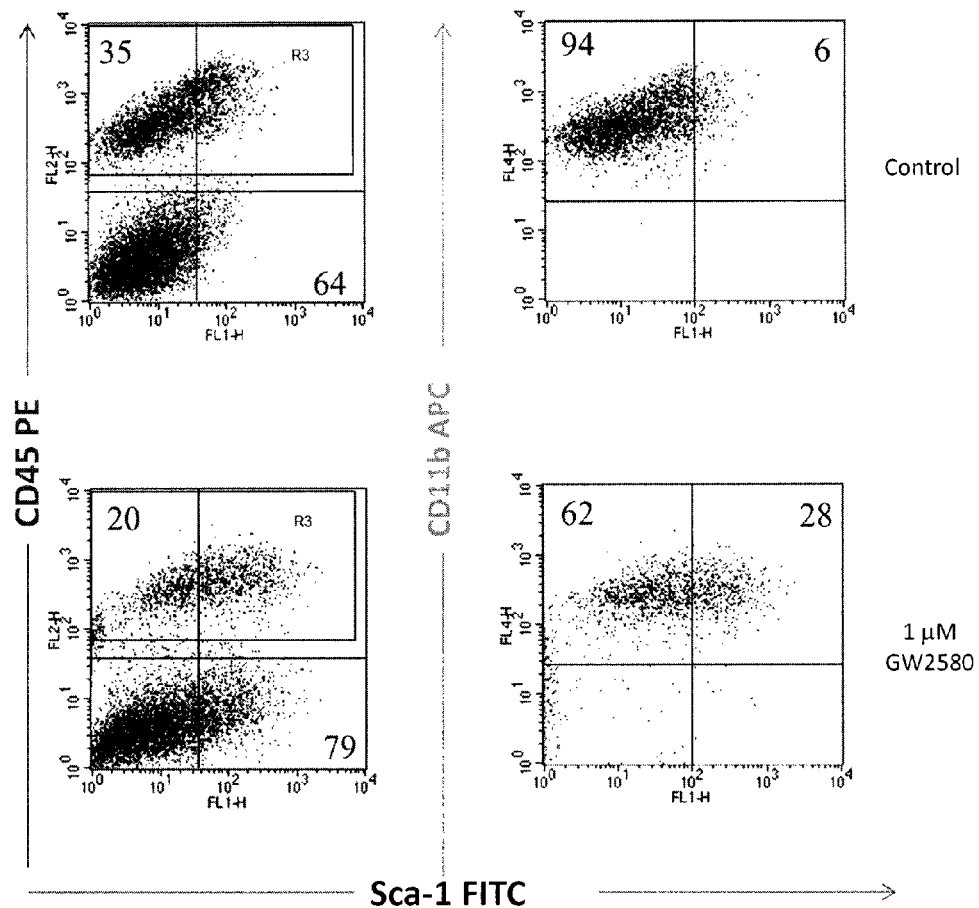
FIG. 9 shows that exposure of CB-derived cultures to 1 μM GW2580 from P0 to P2 leads to an overall 15% reduction in CD45$^+$ cells and a 22% reduction in CD45$^+$/CD11b$^+$/Sca1$^+$ hematopoietic monocyte differentiation into CD45$^+$/CD11b$^+$/Sca1$^-$ mature macrophage as demonstrated by flow cytometry analysis. Cultures were gated on CD45$^+$ cells and, out of this population, expression of CD11b and Sca1 was analyzed. In control cultures, 94% of the CD45$^+$ cells were also CD11b$^+$ (differentiated macrophages) and 6% of the cells were CD11b$^+$/Sca1$^+$ hematopoietic monocytes. In GW2580-treated cultures, 62% of the CD45$^+$ cells were CD11b$^+$/Sca1$^-$ and 28% of the cells were CD11b$^+$/Sca1$^+$, thus suggesting that 22% of monocytes did not differentiate into macrophages when compared to control cultures.
Figure 10:
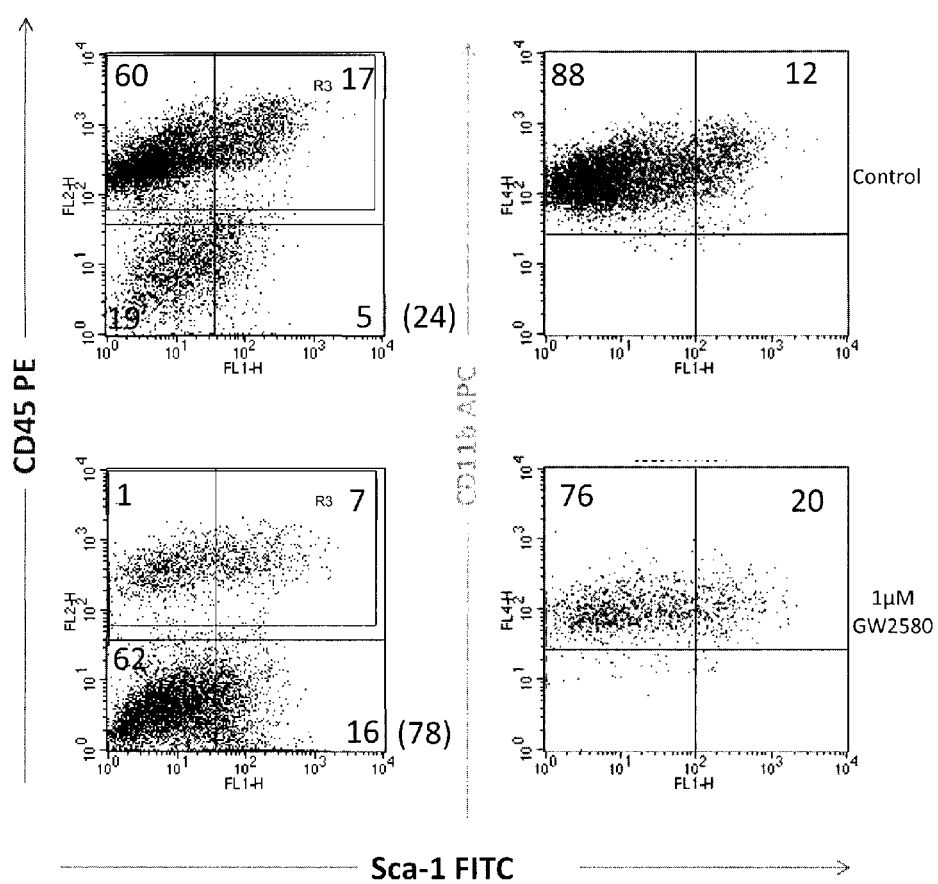
FIG. 10 shows that exposure of CB-derived cultures to 1 μM GW2580 from P0 to P3 leads to an overall 55% reduction in CD45$^+$ cells and a 8% reduction in CD45$^+$/CD11b$^+$/Sca1$^+$ hematopoietic monocyte differentiation into CD45$^+$/CD11b$^+$/Sca1$^-$ macrophage as demonstrated by flow cytometry analysis. Cultures were gated on CD45$^+$ cells and, out of this population, expression of CD11b and Sca1 was analyzed. In control cultures, 88% of the CD45$^+$ cells were also CD11b$^+$ (differentiated macrophages) and 12% of the cells were CD11b$^+$/Sca1$^+$ (hematopoietic monocyte). In GW2580-treated cultures, 76% of the CD45$^+$ cells were CD11b$^+$/Sca1$^-$ and 20% of the cells were CD11b$^+$/Sca1$^+$, thus suggesting that 8% of monocytes did not differentiate into macrophages when compared to control cultures.

Flow cytometry analysis was performed as indicated above. Samples were gated on viable $CD45^+$ cells and analysis of CB-derived cultures at P2 demonstrated that in control cultures, 94% of the CD45$^+$ cells are also CD11b$^+$ mature macrophages, and only 6% maintain a CD45$^+$/CD11b$^+$/Sca1$^+$ hematopoietic monocyte phenotype. Cultures treated with 1 μM GW2580, show that 62% of CD45$^+$ cells are also CD11b$^+$ mature macrophages, and that 28% of them maintain a CD45$^+$/CD11b$^+$/Sca1$^+$ hematopoietic monocyte phenotype. Thus, these results indicate that in CB-derived cultures treated with 1 μM GW2580, there is a 22% increase in CD45$^+$/CD11b$^+$ that were also Sca1$^+$. This suggests that treatment of these cultures with 1 μM GW2580 prevented macrophage differentiation into CD45$^+$/CD11b$^+$/Sca1$^-$ (FIG. 9). At P3, treatment of these cultures with 1 μM GW2580 led to a 12% reduction in CD45$^+$/CD11b$^+$/Sca1$^-$ mature macrophage differentiation and a 8% increase in Sca1$^+$ cells. These results suggest that treatment of CB-derived cultures with 1 μM GW2580 prevented a small proportion of CD45$^+$/CD11b$^+$/Sca1$^+$ hematopoietic monocyte from differentiating into CD45$^+$/CD11b$^+$/Sca1$^-$ mature macrophages when compared to control cultures (FIG. 10).

Figure 8:
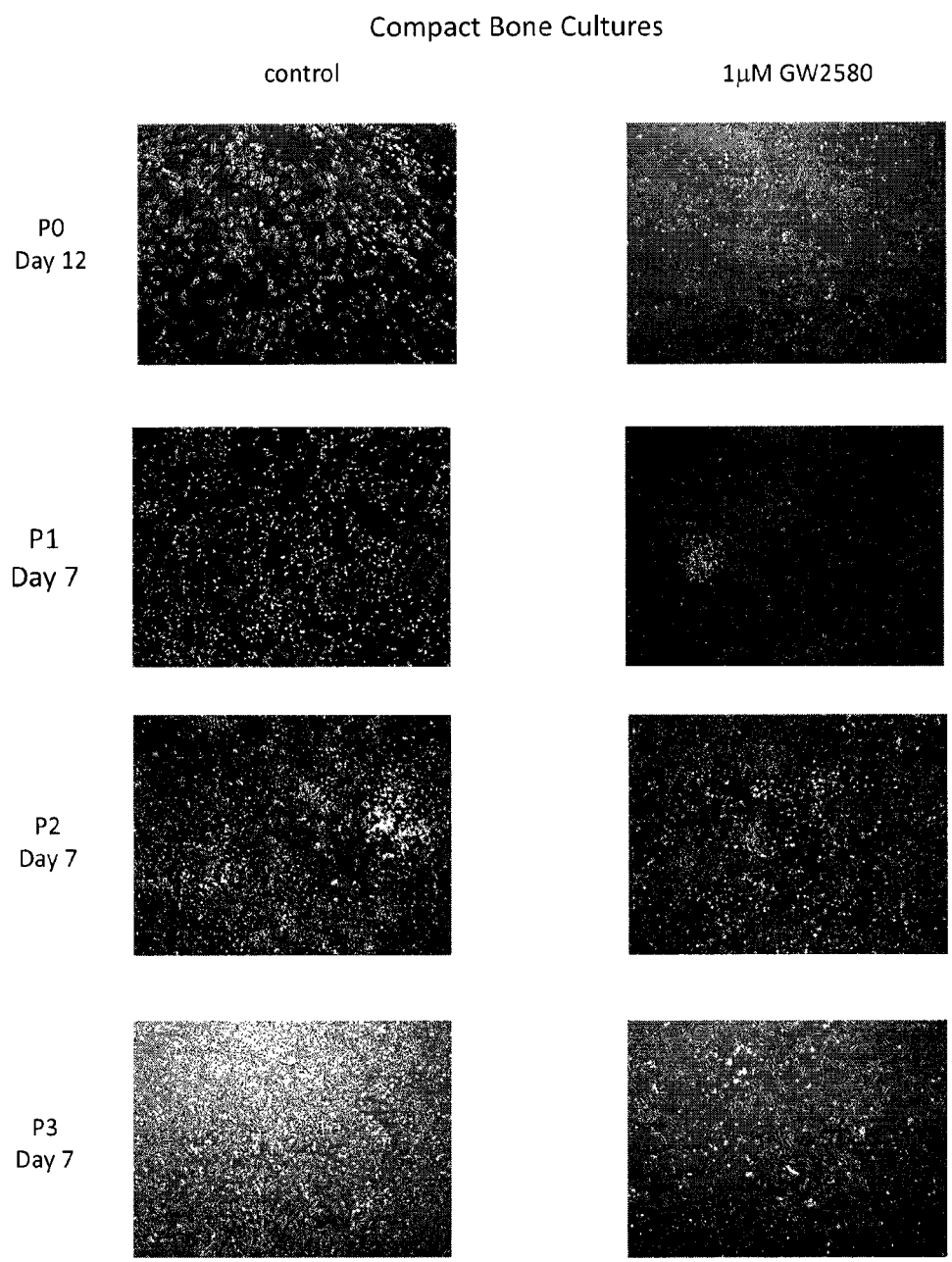
FIG. 8 shows that continuous treatment of CB cultures with 1 μM GW2580 throughout passages (P0-P3) greatly reduces the number of macrophages while maintaining an enriched population of MSC. Control cultures show a high number of small, refractile contaminating macrophages, whereas cultures treated with 1 μM GW2580 contain a much reduced number of these contaminating macrophages. In addition, GW2580-treated cultures display more abundant numbers of fibroblast-like cells that are characteristic of MSC.

Taken together, these results demonstrate that treatment of CB-derived cultures with 1 μM GW2580 prevented differentiation of CD45$^+$/CD11b$^+$/Sca1$^+$ hematopoietic monocytes into CD45$^+$/CD11b$^+$/Sca1$^-$ mature macrophages (FIGS. 9 and 10), which in turn resulted in an enriched MSC culture (FIG. 8).

Figure 11:
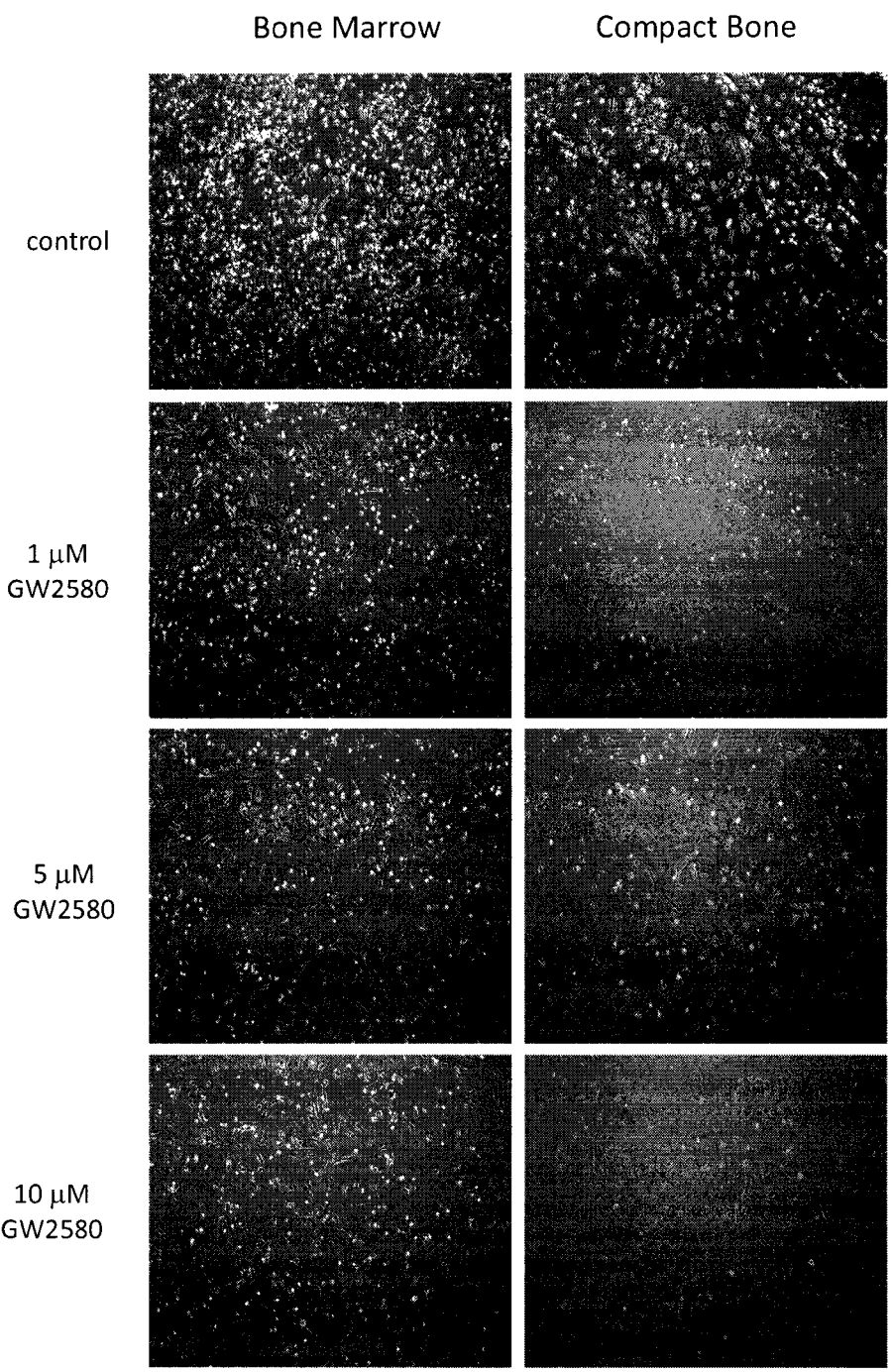
FIG. 11 shows that addition of GW2580 in a concentration ranging from 1 to 10 μM to BM or CB cultures reduces macrophage contamination in culture and has no negative effect on MSC population. Cultures of BM or CB-derived cells were exposed to 1, 5, and 10 μM GW2580 and, regardless of the concentration used, a noticeable decrease in macrophages was noticed and MSCs displayed a healthy fibroblastic appearance when compared to control cultures.
Figure 12:
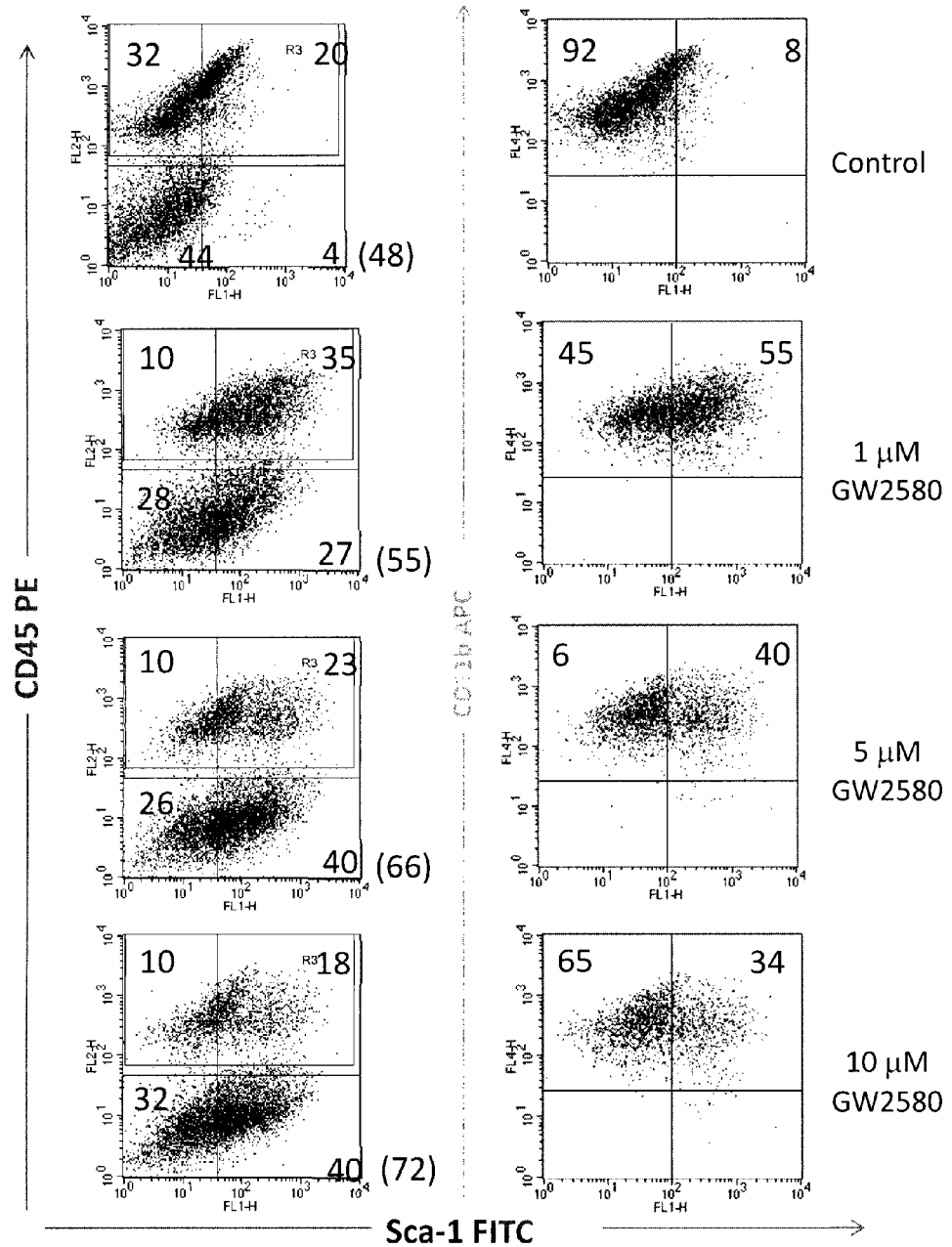
FIG. 12 shows that exposure of BM-derived cultures to 1, 5, or 10 μM GW2580 leads to a dose-responsive decrease in CD45$^+$ and also hematopoietic monocytes. The number of CD45$^+$ was reduced from 52% in control cultures to 45%, 33%, and 28% in cultures treated with 1, 5, and 10 μM GW2580, respectively. Unexpectedly, the number of CD45$^+$/CD11b$^+$/Sca1$^+$ also decreased in a dose-responsive manner from 55%, to 40%, to 34% in cultures treated with 1, 5, and 10 μM GW2580, respectively.

Example 10: Exposure of Expansion Cultures of Mouse BM and CB-Derived Cells to Increasing Concentrations Ranging from 1 to 10 μM GW2580 Leads to Increasing Prevention of Macrophage Differentiation and Increasing Enrichment of MSC in Culture in a Concentration-Dependent Manner in CB-Derived Cultures, but not in BM-Derived Cultures BM and CB-derived cultures were isolated as described above and expansion assays setup as described above. Assays were maintained in medium containing 0.1% v/v DMSO as control or treated with 1, 5, or 10 μM GW2580. Images of cultures show that control cultures are overgrown with contaminating macrophages, while cultures treated with 1, 5, or 10 μM GW2580 have reduced numbers of contaminating macrophages. In addition, most of the adherent cells in both BM and CB-derived cultures display a healthy fibroblastic morphology typical of MSC when compared to control cultures (FIG. 11).

Flow cytometry analysis was performed as indicated above. Samples were gated on viable CD45$^+$ cells which were reduced from 52% in control cultures to 45%, 33%, and 28% in cultures treated with 1, 5, and 10 μM GW2580, respectively. Further, 92% of the CD45$^+$ cells were also CD11b$^+$ mature macrophages, and only 8% maintained a CD45$^+$/CD11b$^+$/Sca1$^+$ monocyte phenotype in control cultures. Unexpectedly, the number of CD45$^+$/CD11b$^+$/Sca1$^+$ also decreased in a dose-responsive manner from 55%, to 40%, to 34% in cultures treated with 1, 5, and 10 μM GW2580, respectively.

Figure 13:
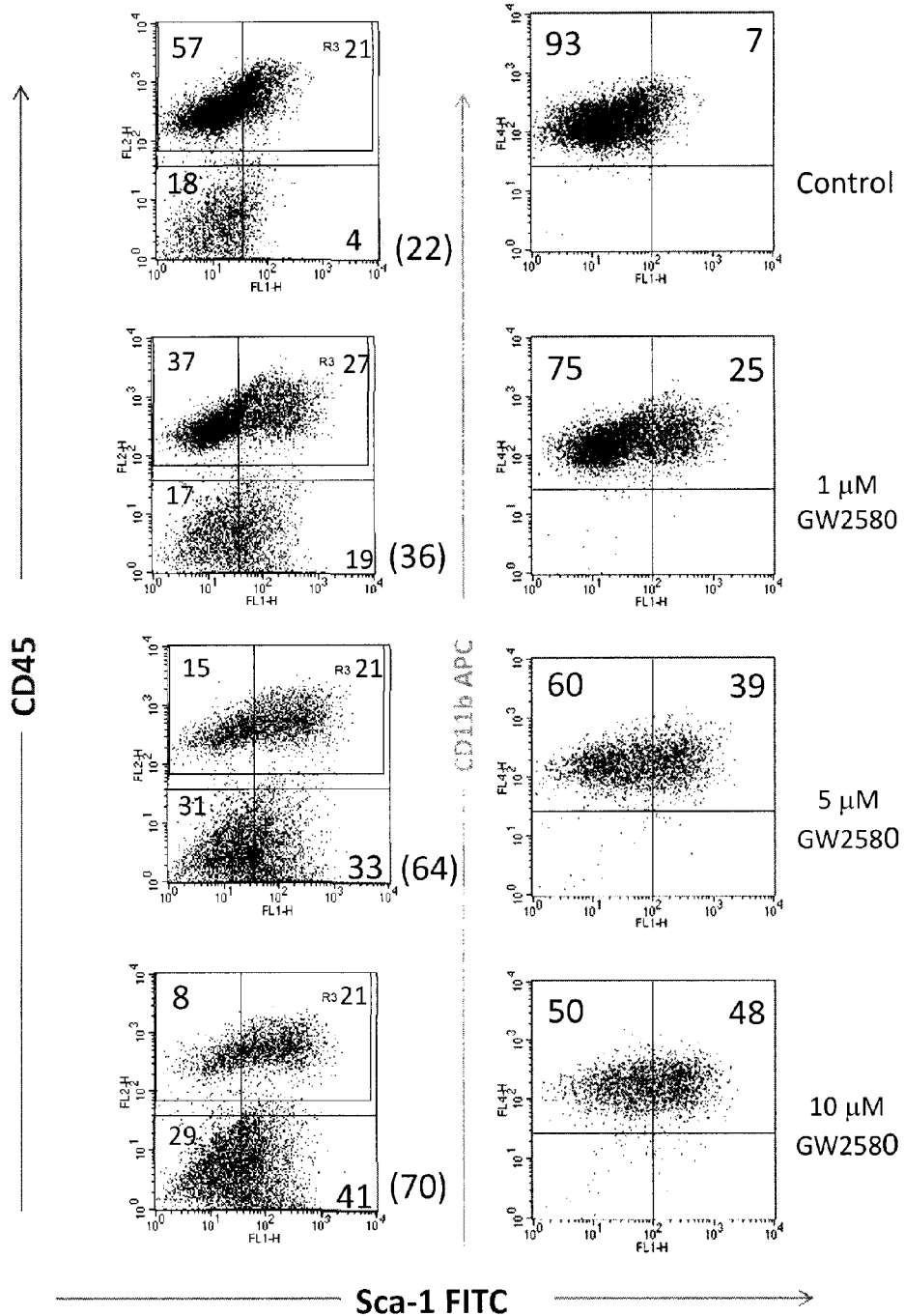
FIG. 13 shows that exposure of CB-derived cultures to 1, 5, or 10 μM GW2580 leads to a dose-responsive reduction in CD45$^+$/CD11b$^+$/Sca1$^-$ mature macrophages while displaying a similar dose-responsive increase in CD45$^+$/CD11b$^+$/Sca1$^+$ monocytes. The number of CD45$^+$ was reduced from 78% in control cultures to 64%, 36%, and 30% in cultures treated with 1, 5, and 10 μM GW2580, respectively. The number of CD45$^+$/CD11b$^+$/Sca1$^+$ monocytes increased in a dose-responsive manner from 7% in control cultures, to 25%, 39%, and 48% in cultures treated with 1, 5, and 10 μM GW2580, respectively.

Flow cytometry analysis of CB-derived cultures demonstrated that in control cultures, 93% of the CD45$^+$ cells are CD11b$^+$ mature macrophages, and only 7% maintained a CD45$^+$/CD11b$^+$/Sca1$^+$ hematopoietic monocyte phenotype. Cultures treated with 1, 5, or 10 μM GW2580 show a dose-response decrease in CD45$^+$/CD11b$^+$ mature macrophages from 75 to 60 and to 50%, respectively. This decrease in macrophage differentiation translated into a dose-response increase in CD45$^+$/CD11b$^+$/Sca1$^+$ hematopoietic monocytes from 18 to 32 and to 41%, respectively. Thus, these results indicate that in CB-derived cultures treated with a range of GW2580 concentrations, there was a 26 to 47% increase in CD45$^+$/CD11b$^+$ cells that were also Sca1$^+$. This suggests that treatment of these cultures with increasing concentrations of 1, 5, and 10 μM GW2580 prevented macrophage differentiation (CD45$^+$/CD11b$^+$/Sca1$^-$) in a dose-dependent manner (FIG. 13).

Figure 14:
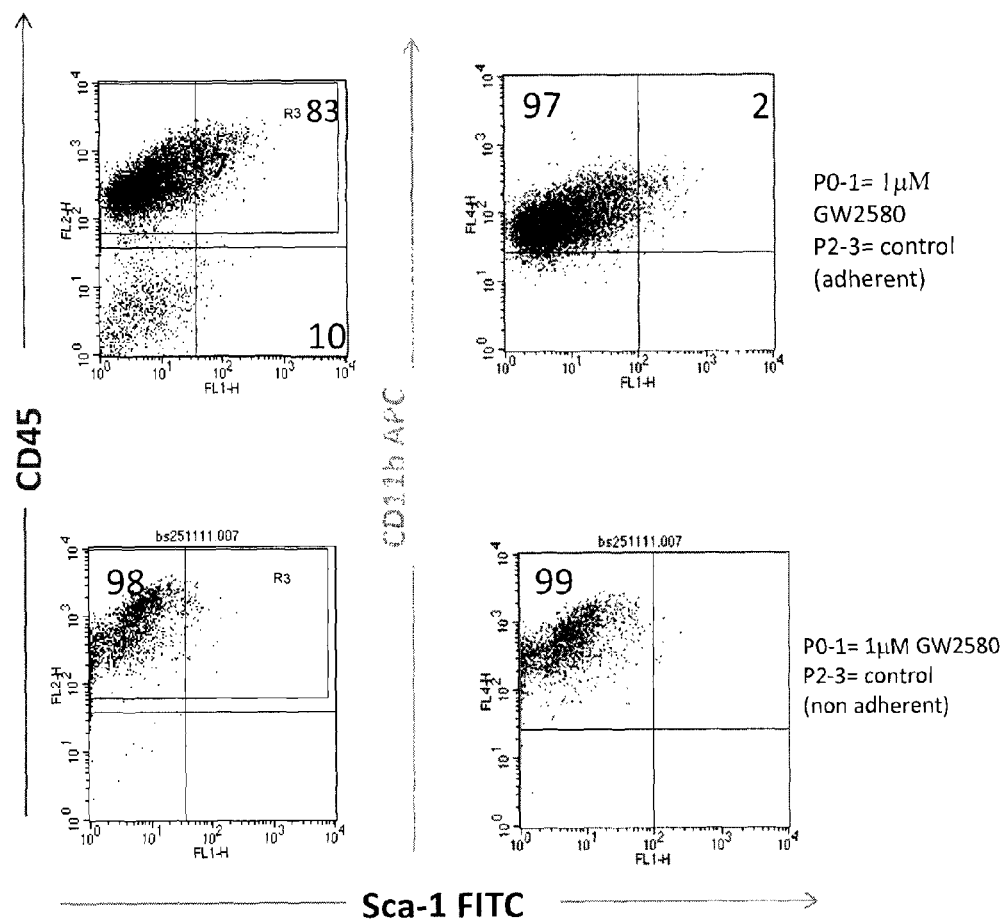
FIG. 14 shows that early removal of GW2580 at P2 leads to reappearance of macrophages in CB cultures. CB bone cultures were maintained in the presence of 1 μM GW2580 for 2 passages (P0-P1) following 2 more passages (P2-P3) in the presence of vehicle. Flow cytometry analysis was performed at P3. Cultures were gated on CD45$^+$ cells and, out of this population, expression of CD11b and Sca1 was analyzed. Analysis revealed that 97% of CD45$^+$ cells were CD45$^+$/CD11b$^+$/Sca1$^-$ mature macrophages and only 2% remained as CD45$^+$/CD11b$^+$/Sca1$^+$ monocytes in adherent cultures. In non-adherent cultures, 99% of CD45$^+$ cells were CD45$^+$/CD11b$^+$/Sca1$^-$ mature macrophages and <1% remained as CD45$^+$/CD11b$^+$/Sca1$^+$ monocytes.

Example 11: Continuous Treatment of Expansion Cultures of CB-Derived Cells with 1 μM GW2580 is Necessary to Prevent Macrophage Differentiation and Proliferation CB-derived cultures were isolated as described above and expansion assays setup as described above. Assays were maintained in medium containing 1 μM GW2580 during passages P0 to P1 and then maintained in control medium containing 0.1% v/v DMSO during P2 to P3. At the end of P3, adherent and non-adherent cells were collected and flow cytometry analysis was performed as indicated above. Samples were gated on viable CD45$^+$ cells and analysis of adherent and non-adherent cells demonstrated that 97% of the adherent cells and 99% of the non-adherent cells were CD45$^+$/CD11b$^+$/Sca1$^-$ mature macrophage. These results suggest that continuous exposure to 1 μM GW2580 is necessary to prevent macrophage differentiation in culture (compare FIG. 14 to control treatment in FIG. 10).

Example 12: Treatment of CB-Derived Cultures with 1 μM GW2580 During P3 to P4 is as Effective in Reducing the Number of CD45$^+$/CD11b$^+$ Mature Macrophages while Maintaining MSCs in Culture as Enriching these Cultures Using the EasySep Isolation of Mesenchymal Progenitors from Mouse Compact Bone (STEMCELL Catalogue #19771)

Figure 15:
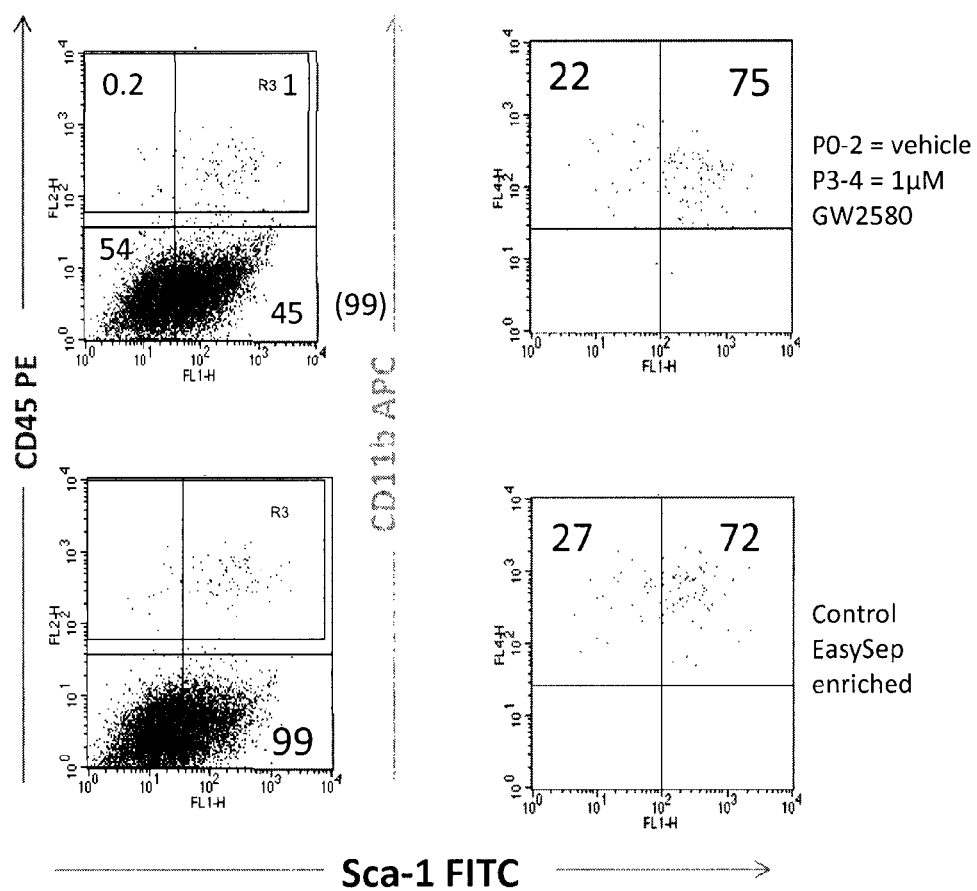
FIG. 15 shows CB-derived cultures that were maintained in control medium containing 0.1% v/v DMSO during passages P0 to P2 and then maintained in medium containing 1 μM GW2580 during P3 to P4. For comparative purposes, P4 control cultures were enriched for mesenchymal progenitors using the EasySep Isolation of Mesenchymal Progenitors From Mouse Compact Bone (STEMCELL). Samples were gated on viable CD45$^+$ cells, which in GW2580-treated and EasySep-enriched samples comprised <0.2% of total cells. Out of these CD45$^+$ cells only around 25% of the cells were CD11b$^+$/Sca1 mature macrophages in both cultures, whereas about 75% of the CD45$^+$ cells were CD11$^+$/Sca1$^+$ monocytes.

CB-derived cultures were isolated as described above and expansion assays setup as described above. Cultures were maintained in control medium containing 0.1% v/v DMSO during passages P0 to P2 and then maintained in medium containing 1 μM GW2580 during P3 to P4. For comparative purposes, P4 control cultures were enriched for mesenchymal progenitors using the EasySep Isolation of Mesenchymal Progenitors From Mouse Compact Bone (STEMCELL catalogue #19771) as per manufacturer's instruction. Cells were collected and flow cytometry analysis was performed as indicated in above. Samples were gated on viable CD45$^+$ cells, which in GW2580-treated and EasySep-enriched samples comprised <0.2% of total cells. Out of these CD45$^+$ cells only around 25% of the cells were CD11b$^+$/Sca1$^-$ mature macrophages in both samples. In addition, in both samples about 75% of the CD45$^+$ cells were CD11$^+$/Sca1$^+$ hematopoietic monocytes (FIG. 15).

These results suggest that treatment of CB-derived cultures with 1 μM GW2580 is as effective in reducing CD45$^+$/CD11b/Sca1$^-$ mature macrophages from the culture as using the EasySep enrichment system.

Example 13: Treatment of BM and CB-Derived Cultures with 1 μM KI20227 is as Effective as Treatment with 1 μM GW2580 in Reducing the Number of CD45$^+$/CD11b$^+$ Mature Macrophages in Culture BM and CB-derived cultures were isolated as described above and expansion assays setup as described above.

Figure 16:
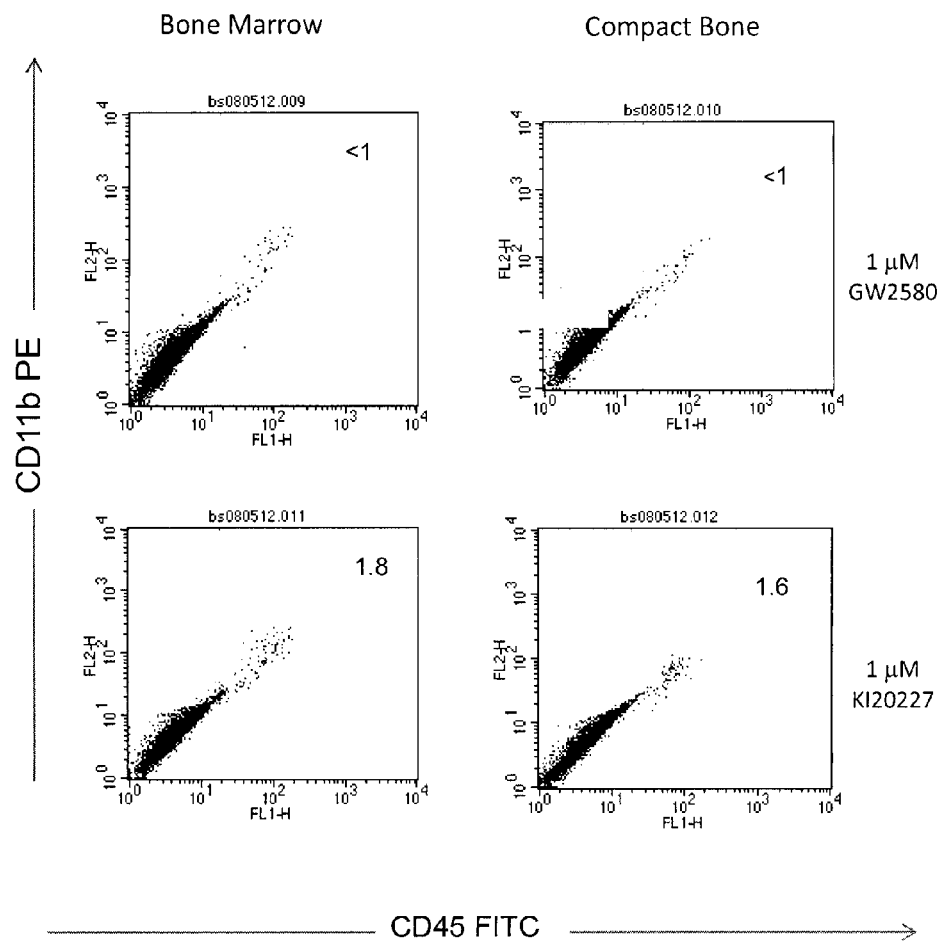
FIG. 16 shows that treatment of BM and CB-derived cultures with either 1 μM GW2580 or 1 μM KI20227 leads to a similar reduction in CD45$^+$/CD11b$^+$ mature macrophages indicating that this activity is due CSF1R receptor inhibition.

Cultures were maintained in medium containing 1 μM KI20227 or in medium containing 1 μM GW2580 up to P2. Cells were collected and flow cytometry analysis was performed as indicated above. Samples were gated on viable cells, and analysis show that in GW2580-treated cultures, <1% of the cells were $CD45^+/CD11b^+$ mature macrophages. In KI20227-treated cultures, <2% were $CD45^+/CD11b^+$ mature macrophages (FIG. 16).

Without being bound by theory, these results suggest that inhibition of macrophage proliferation and differentiation in BM and CB-derived cultures is not limited to GW2580, but instead is an activity observed with this class of CSF1R receptor inhibitors.

Figure 17:
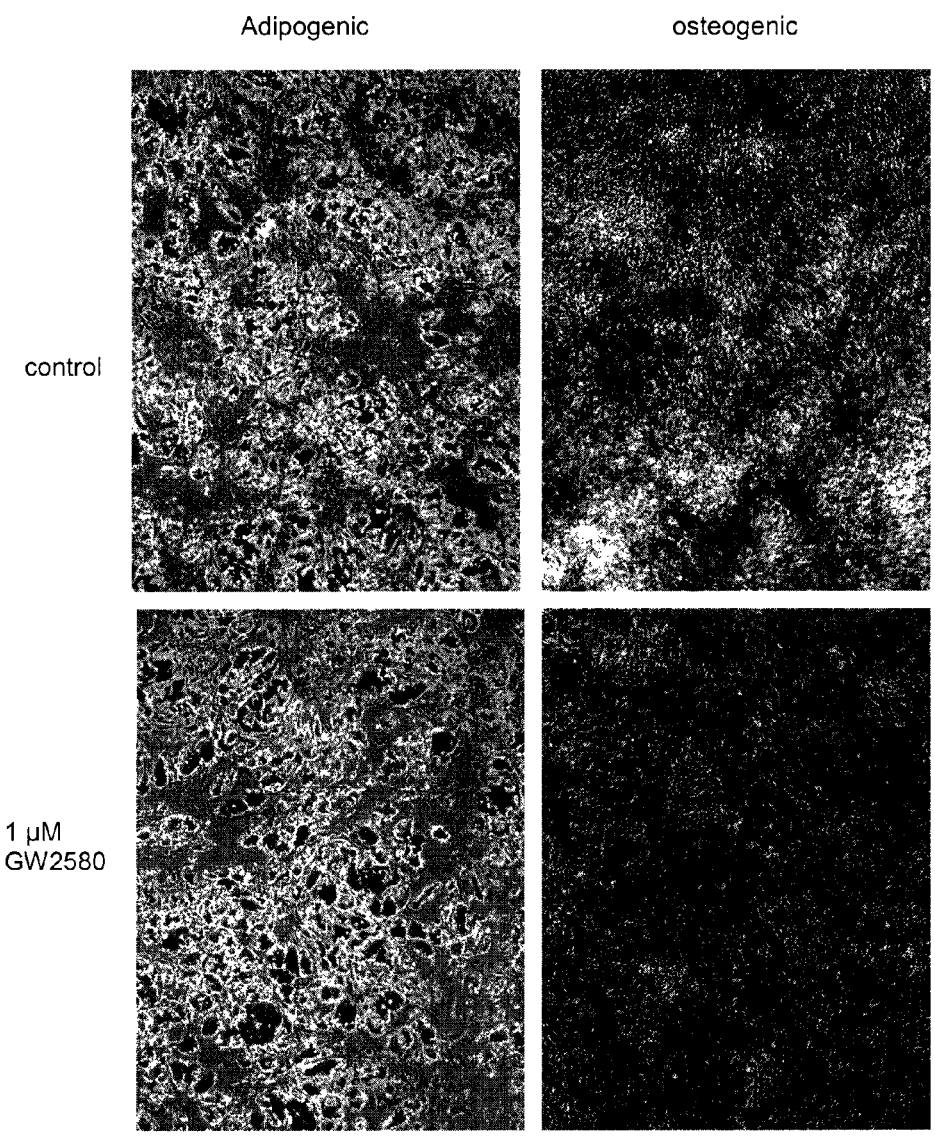
FIG. 17 shows human BM-derived MSCs that were expanded up to P2 in control medium or medium containing 1 μM GW2580 and then exposed to adipogenic and osteogenic differentiation media for 3 weeks. Adipogenic cultures were fixed and stained with Oil red O. Osteogenic cultures were fixed and stained with silver nitrate. Both control and GW2580-treated cultures differentiated equally well suggesting that GW2580 does not affect the ability of MSCs to differentiate.

Example 14: Treatment of Human BM-Derived MSC Cultures with 1 μM GW2580 does not Hinder the Differentiation Potential of these Cells BM-derived cultures were isolated as described above and expansion assays setup as described above. These P2 expansion cultures were maintained in control medium containing 0.1% v/v DMSO or in medium containing 1 μM GW2580. At the end of P2, cell were dissociated by trypsin digestion and replated at $3\times10^4$ cells/cm$^2$ in 12-well plates for differentiation assays. Differentiation cultures were maintained for 3 weeks in adipogenic or osteogenic differentiation media. At the end of the 3-week period, cultures were fixed and stained with Oil red O to assess adipogenic differentiation, or with silver nitrate to assess osteogenic differentiation. Cultures that were expanded in the presence of 1 μM GW2580 show similar levels of adipogenic and osteogenic differentiation as cultures that were expanded in control medium (FIG. 17).

These results demonstrate that exposure of BM-derived MSC cultures to 1 μM GW2580 does not hinder their ability to differentiate.

Example 15: CFU-F Assays of BM- and CB-MSC Exposed to GW2580 for 14 Days Show an Increase in the Number of MSC Colonies in Culture Three independent assays CFU-F assays for both BM- and CB-MSC were setup as in Example 4a and 4b. In assay 1, cultures were exposed to 1 uM GW2580 or vehicle control. In assays 2 and 3, cultures were exposed to 2.5 uM GW2580 or vehicle control. These assays were maintained for 14 days without media change. At the end of day 14, cultures were fixed and stained with toluidine blue and the number of MSC colonies counted. In these assays, exposure of primary cultures of BM- or CB-MSC to 1 or 2.5 uM GW2580 for 14 days led to an overall minimum increase of 20% in the number of MSC colonies observed in CFU-F assays when compared to control cultures (Table 1), This suggests that GW2580 not only enriches for MSCs by reducing the number of hematopoietic cells, but also enhances MSC self-renewal.

Example 16: BM- and CB-MSC Cultures Show a Significant Enrichment in CD45$^-$ Cells with an Increase in CD29$^+$/Sca1$^+$ Cells when Exposed to 2.5 uM GW2580 for 14 Days During P0

In addition to enrichment of the CD45$^-$ cell population by reduction of the CD45$^+$ population observed in MSC cultures exposed to 2.5 uM GW2580, a total cell count analysis in association to flow cytometry was performed to investigate the actual number of MSCs in culture. Prior to flow cytometry, control and GW2580-treated cultures of BM- and CB-MSC were dissociated from tissue culture flasks by trypsinization and the total number of cells counted with the aid of a hemocytometer. Flow cytometry analysis was performed and the ratio of CD45$^-$ cells and CD45$^-$/CD29$^+$/Sca1$^+$ cells applied to the total number of cells to obtain the actual number of these cells in culture (Table 2). This analysis revealed that in BM-MSC cultures, there was a marginal increase in the number CD45$^-$ cells from 632,800 in control cultures to 665,331 in cultures exposed to GW2580 (fold-induction from control cultures reported in brackets). However, the CD45$^-$/CD29$^+$/Sca1$^+$ fraction increased from 473,841 cells in control cultures to 639,450 cells in GW2580-treated cultures, an actual increase of 0.25-fold in BM-MSCs in cultures exposed to GW2580. In CB-MSC cultures, an appreciable increase from 206,400 cells in control cultures to 530,702 cells in GW2580-exposed cultures was observed, resulting in a 2.57-fold increase in the actual number of CD45$^-$ cells. Similarly, in this culture system, a 2.46-fold increase in CD45$^-$/CD29$^+$/Sca1$^+$ MSCs was obtained when CB-MSCs were exposed to GW2580. Taken together, these results suggest that GW2580 enriches for MSCs in cultures by removal of unwanted hematopoietic CD45$^+$ cells, while substantially increasing expansion of CD45$^-$/CD29$^+$/Sca1$^+$ MSCs.

Figure 18:
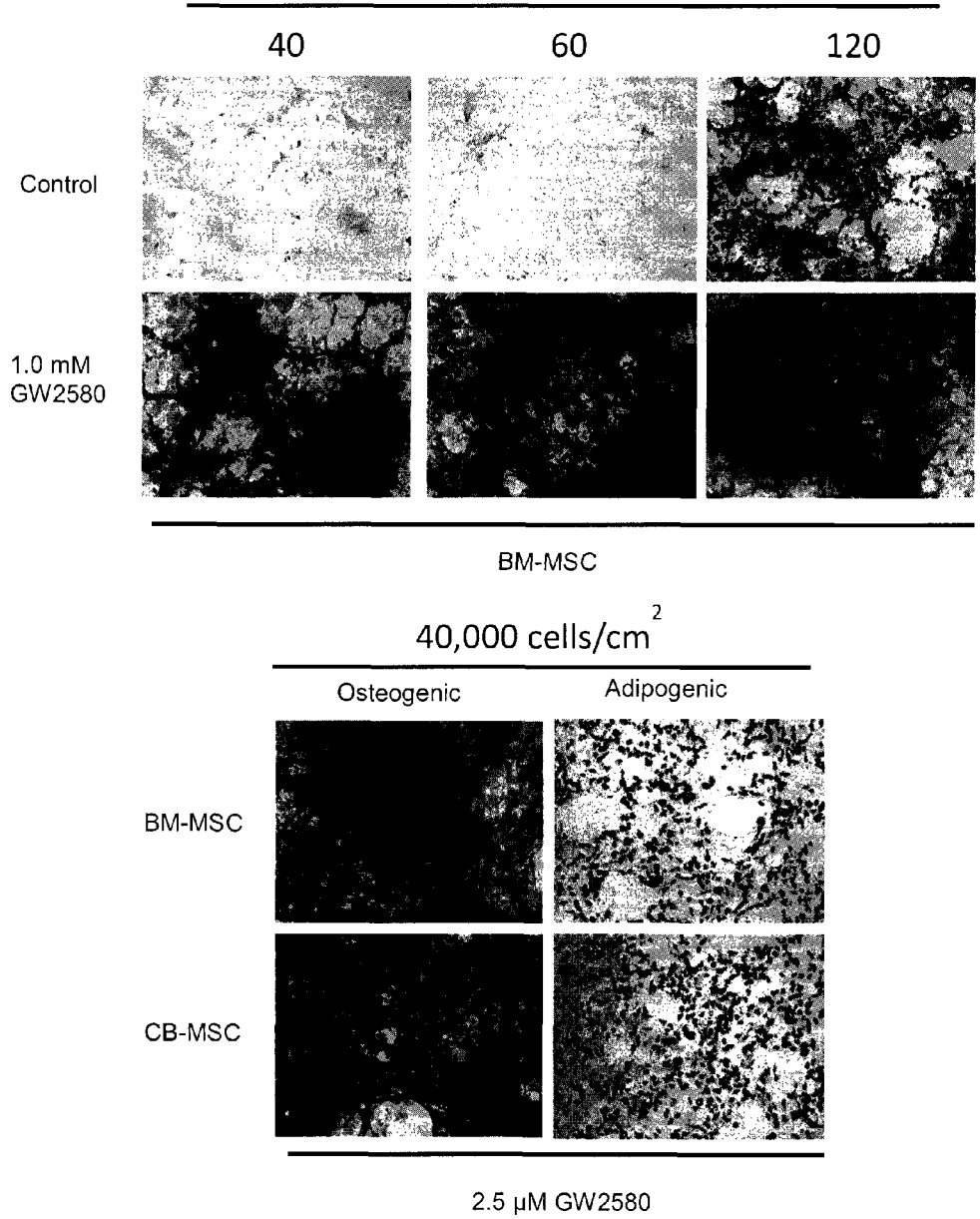
FIG. 18 shows that exposure of mouse BM- and CB-MSC cultures to GW2580 during expansion led to stronger and more robust differentiation into the osteogenic and adipogenic lineages than control cultures and required fewer cells.

Example 17: Exposure of BM- and CB-MSC Cultures to GW2580 During Expansion Facilitates Downstream Differentiation of these Cells and Requires Fewer Cells than Cultures Exposed to a Vehicle Control During the process of culture, expansion, or maintenance of MSCs, it is imperative that these cells maintain their functional properties so they can be used for specific downstream applications, including characterization by differentiation. To demonstrate that exposure of BM- and CB-MSC cultures to GW2580 does not affect their ability to differentiate, BM- and CB-MSC cultures were maintained in control medium or in medium containing GW2580 for 2 passages and then plated at different densities for differentiation into the osteogenic and adipogenic lineages (FIG. 18). BM-MSCs that were initially exposed to vehicle- or GW2580-containing media were plated at 3 different densities (FIG. 18A) in MesenCult Proliferation Medium and allowed to adhere to the plates overnight. Cultures were then differentiated for 14 days in MesenCult Osteogenic Medium, and the medium changed every 3 days. Osteogenic cultures were then fixed and stained for alkaline phosphates (ALP) activity (red areas) and mineralization (black areas). In control cultures (FIG. 8A), a modest differentiation into the osteogenic lineage was only observed when cultures were seeded at the highest density of $1.2\times10^5$ cells/cm$^2$. In cultures exposed to 1 uM GW2580, however, a significant and robust increase in osteogenic differentiation was observed in cultures seeded at a low density of $4.0\times10^4$ cells/cm$^{2\prime}$ as demonstrated by the red areas (ALP activity) and staining of mineralized bone matrix (black areas). In a similar assay, both BM- and CB-MSC were expanded for 2 passages in the presence of 2.5 uM GW2580 and then plated at $4.0\times10^4$ cells/cm$^2$. Cultures were then differentiated for 14 days into the adipogenic and osteogenic lineages (FIG. 18B). A substantial adipogenic and osteogenic differentiation was observed in these cultures as demonstrated by Oil Red O and ALP/mineralization staining, respectively. Taken together, these data suggest that exposure of BM- and CB-MSC cultures to GW2580 facilitates their ability to strongly differentiate into different lineages, likely due to the enrichment and increased proliferation of MSC observed in cultures exposed to GW2580 when compared to control cultures.

TABLE 1

| Assay Number | Number of cells plated | Number of MSC colonies | | |
|---|---|---|---|---|
| | | control | GW2580 | % increase |
| BM-MSC | | | | |
| 1 | $2.5 \times 10^5$ | 82 | 103 | 26 |
| | $5.0 \times 10^5$ | 140 | 201 | 44 |
| | $1.0 \times 10^6$ | 180 | 227 | 26 |
| | Sum | 402 | 531 | 32 |
| 2 | $2.5 \times 10^5$ | 4 | 3 | 0 |
| | $5.0 \times 10^5$ | 11 | 23 | 109 |
| | $1.0 \times 10^6$ | 28 | 34 | 21 |
| | Sum | 43 | 60 | 40 |
| 3 | $2.5 \times 10^5$ | 3 | 5 | 67 |
| | $5.0 \times 10^5$ | 10 | 17 | 70 |
| | $1.0 \times 10^6$ | 40 | 60 | 50 |
| | Sum | 53 | 82 | 55 |
| CB-MSC | | | | |
| 1 | $5.0 \times 10^4$ | 27 | 46 | 70 |
| | $1.0 \times 10^5$ | 51 | 77 | 51 |
| | $2.5 \times 10^5$ | 102 | 133 | 30 |
| | Sum | 180 | 256 | 42 |
| 2 | $2.5 \times 10^5$ | 12 | 15 | 25 |
| | $5.0 \times 10^5$ | 33 | 36 | 9 |
| | $1.0 \times 10^6$ | 45 | 83 | 84 |
| | Sum | 90 | 134 | 49 |
| 3 | $2.5 \times 10^5$ | 28 | 35 | 25 |
| | $5.0 \times 10^5$ | 69 | 89 | 29 |
| | $1.0 \times 10^6$ | 80 | 147 | 84 |
| | Sum | 177 | 271 | 53 |

TABLE 2

| | | Percent (Flow Cytometry) | | |
|---|---|---|---|---|
| | | total cells | CD45− | CD45−/CD29+/Scal+ |
| BM-MSCs | ctrl | 7.00E+06 | 9.04 | 74.88 |
| | MesenPure | 9.44E+05 | 70.48 | 96.11 |
| CB-MSCs | ctrl | 3.00E+06 | 6.38 | 79.66 |
| | MesenPure | 5.56E+05 | 95.45 | 95.65 |

| | | Actual number of cells | |
|---|---|---|---|
| | | CD45− | CD45−/CD29+/Scal+ |
| BM-MSCs | ctrl | 632,800 (1.00) | 473,841 (0.75) |
| | MesenPure | 665,331 (1.05) | 639,450 (1.01) |
| Ca-MSCs | ctrl | 206,400 (1.00) | 164,418 (0.80) |
| | MesenPure | 530,702 (2.57) | 507,616 (2.46) |

REFERENCES

1. Yu W., Chen J., Xiong Y., Pixley F. J., Yeung Y. G., Stanley E. R. Macrophage proliferation is regulated through CSF-1 receptor tyrosines 544, 559, and 807. J Biol Chem. 2012; 287(17):13694-704.
2. Tagliani E., Shi C., Nancy P., Tay C. S., Pamer E. G., Erlebacher A. Coordinate regulation of tissue macrophage and dendritic cell population dynamics by CSF-1. J Exp Med. 2011; 208(9):1901-16.
3. Conway J G, McDonald B, Parham J, Keith B, Rusnak D W, Shaw E, Jansen M, Lin P, Payne A, Crosby R M, Johnson J H, Frick L, Lin M H, Depee S, Tadepalli S, Votta B, James I, Fuller K, Chambers T J, Kull F C, Chamberlain S D, Hutchins J T. Inhibition of colony-stimulating-factor-1 signaling in vivo with the orally bioavailable cFMS kinase inhibitor GW2580. Proc Natl Acad Sci USA. 2005; 102(44):16078-83.
4. Pixley F J, Stanley E R. CSF-1 regulation of the wandering macrophage: complexity in action. Trends Cell Biol. 2004; 14(11):628-38.
5. Dewar A L, Cambareri A C, Zannettino A C, Miller B L, Doherty K V, Hughes T P, Lyons A B. Macrophage colony-stimulating factor receptor c-fms is a novel target of imatinib. Blood. 2005; 105(8):3127-32.
6. Bourette R P, Rohrschneider L R. Early events in M-CSF receptor signaling. Growth Factors. 2000; 17(3):155-66.
7. Kaplan R N, Psaila B, Lyden D. Niche-to-niche migration of bone-marrow-derived cells. Trends Mol Med. 2007; 13(2):72-81.
8. Yin T, Li L. The stem cell niches in bone. J Clin Invest. 2006; 116(5):1195-201.
9. Lo Celso C, Scadden D T. The haematopoietic stem cell niche at a glance. J Cell Sci. 2011; 124 (Pt 21):3529-35.
10. Wilson A, Trumpp A. Bone-marrow haematopoietic-stem-cell niches. Nat Rev Immunol. 2006; 6(2):93-106.
11. Hume D A, Pavli P, Donahue R E, Fidler I J. The effect of human recombinant macrophage colony-stimulating factor (CSF-1) on the murine mononuclear phagocyte system in vivo. J Immunol. 1988; 141(10):3405-9.
12. Wiktor-Jedrzejczak W, Bartocci A, Ferrante A W Jr, Ahmed-Ansari A, Sell K W, Pollard J W, Stanley E R. Total absence of colony-stimulating factor 1 in the macrophage-deficient osteopetrotic (op/op) mouse. Proc Natl Acad Sci USA. 1990; 87(12):4828-32.
13. Dai X M, Ryan G R, Hapel A J, Dominguez M G, Russell R G, Kapp S, Sylvestre V, Stanley E R. Targeted disruption of the mouse colony-stimulating factor 1 receptor gene results in osteopetrosis, mononuclear phagocyte deficiency, increased primitive progenitor cell frequencies, and reproductive defects. Blood. 2002; 99(1):111-20.
14. Shewchuk, L. M., Hassell, A. M., Holmes, W. D., Veal, J. M., Emmerson, H. K., Musso, D. L., Chamberlain, S. D. & Peckham, G. E. 2004; U.S. Pat. Appl. Publ. 79 pp. US 2004002145.

What is claimed is:

1. A method of increasing the number of mesenchymal cell in a sample comprising cells of the mesenchymal cell lineage and non-mesenchymal cells, said method comprising contacting the sample with a culture media comprising a Colony Stimulating Factor 1 Receptor (CSF1R) kinase inhibitor to increase the number of mesenchymal cells, wherein the method does not require removal of the non-mesenchymal cells prior to adding the CSF1R kinase inhibitor.

2. The method of claim 1, wherein the method comprises:
   a) harvesting cells from a tissue sample obtained from a subject, wherein the harvested cells comprise cells of the mesenchymal cell lineage and non-mesenchymal cells, and
   b) contacting the harvested cells with a culture media comprising a CSF1R kinase inhibitor, and optionally
   c) obtaining a population of cells enriched for cells of the mesenchymal cell lineage.

3. The method of claim 2, wherein the tissue sample comprises bone marrow, compact bone or adipose tissue.

4. The method of claim 1, wherein the CSF1R kinase inhibitor is GW2580, KI20227, HY-13075, cFMS Receptor Inhibitor II, cFMS Receptor Inhibitor III, cFMS Receptor Inhibitor IV or ARRY-382.

5. The method of claim 1, wherein the cells of the mesenchymal cell lineage comprise at least one of a mesenchymal stem cell, a mesenchymal cell progenitor and a stromal-derived cell.

6. The method of claim 1, wherein the cells are contacted with the culture media for at least one hour, at least one day or at least one week.

7. The method of claim 1, wherein prior to contacting the cells with the culture media, the concentration of the cells of the mesenchymal cell lineage is at least 10 cells/cm$^2$.

8. The method of claim 1, wherein the cells of the mesenchymal cell lineage retain their ability to form adipogenic, chrondrogenic and osteogenic cell lineages.

\* \* \* \* \*